US008093431B2

(12) United States Patent
Falana et al.

(10) Patent No.: US 8,093,431 B2
(45) Date of Patent: Jan. 10, 2012

(54) ALDEHYDE-AMINE FORMULATIONS AND METHOD FOR MAKING AND USING SAME

(75) Inventors: Olusegun Matthew Falana, San Antonio, TX (US); Ray Veldman, Bellaire, TX (US); Frank Zamora, San Antonio, TX (US); Emilia U. Ugwu, Univ City, TX (US); Zoraida Vazquez, San Antonio, TX (US)

(73) Assignee: Clearwater International LLC, Houston, TX (US)

( * ) Notice: Subject to any disclaimer, the term of this patent is extended or adjusted under 35 U.S.C. 154(b) by 70 days.

(21) Appl. No.: 12/364,154

(22) Filed: Feb. 2, 2009

(65) Prior Publication Data

US 2010/0197968 A1    Aug. 5, 2010

(51) Int. Cl.
*C07C 209/24* (2006.01)
*C07C 209/60* (2006.01)
(52) U.S. Cl. ......... 564/471; 564/472; 564/473; 564/508
(58) Field of Classification Search ........................ None
See application file for complete search history.

(56) References Cited

U.S. PATENT DOCUMENTS

| | | | |
|---|---|---|---|
| 2,196,042 A | 4/1940 | Timpson | 23/11 |
| 2,390,153 A | 12/1945 | Kern | 260/72 |
| 3,059,909 A | 10/1962 | Wise | 261/39.3 |
| 3,163,219 A | 12/1964 | Wyant et al. | 166/283 |
| 3,301,723 A | 1/1967 | Chrisp | 149/20 |
| 3,301,848 A | 1/1967 | Halleck | 536/123.1 |
| 3,303,896 A | 2/1967 | Tillotson et al. | 175/69 |
| 3,317,430 A | 5/1967 | Priestley et al. | 510/503 |
| 3,565,176 A | 2/1971 | Wittenwyler | 166/270 |
| 3,856,921 A | 12/1974 | Shrier et al. | 423/228 |
| 3,888,312 A | 6/1975 | Tiner et al. | 166/308.5 |
| 3,933,205 A | 1/1976 | Kiel | 166/308.1 |
| 3,937,283 A | 2/1976 | Blauer et al. | 166/307 |
| 3,960,736 A | 6/1976 | Free et al. | 507/216 |
| 3,965,982 A | 6/1976 | Medlin | 166/249 |
| 3,990,978 A | 11/1976 | Hill | 507/235 |
| 4,007,792 A | 2/1977 | Meister | 166/308.2 |
| 4,052,159 A | 10/1977 | Fuerst et al. | |
| 4,067,389 A | 1/1978 | Savins | 166/246 |
| 4,108,782 A | 8/1978 | Thompson | 507/205 |
| 4,112,050 A | 9/1978 | Sartori et al. | 423/223 |
| 4,112,051 A | 9/1978 | Sartori et al. | 423/223 |
| 4,112,052 A | 9/1978 | Sartori et al. | 423/223 |
| 4,113,631 A | 9/1978 | Thompson | 507/202 |
| 4,378,845 A | 4/1983 | Medlin et al. | 166/297 |
| 4,461,716 A | 7/1984 | Barbarin et al. | 252/307 |
| 4,479,041 A | 10/1984 | Fenwick et al. | 200/81 R |
| 4,506,734 A | 3/1985 | Nolte | 166/308.1 |
| 4,514,309 A | 4/1985 | Wadhwa | 507/211 |
| 4,541,935 A | 9/1985 | Constien et al. | 507/225 |
| 4,549,608 A | 10/1985 | Stowe et al. | 166/280.1 |
| 4,561,985 A | 12/1985 | Glass, Jr. | 507/108 |
| 4,623,021 A | 11/1986 | Stowe | 166/250.1 |
| 4,654,266 A | 3/1987 | Kachnik | 428/403 |
| 4,657,081 A | 4/1987 | Hodge | 166/380.5 |
| 4,660,643 A | 4/1987 | Perkins | 166/283 |
| 4,683,068 A | 7/1987 | Kucera | 507/201 |
| 4,686,052 A | 8/1987 | Baranet et al. | 507/244 |
| 4,695,389 A | 9/1987 | Kubala | 507/244 |
| 4,705,113 A | 11/1987 | Perkins | 166/302 |
| 4,714,115 A | 12/1987 | Uhri | 166/308.1 |
| 4,718,490 A | 1/1988 | Uhri | 166/281 |
| 4,724,905 A | 2/1988 | Uhri | 166/250.1 |
| 4,725,372 A | 2/1988 | Teot et al. | 507/129 |
| 4,739,834 A | 4/1988 | Peiffer et al. | 166/308.4 |
| 4,741,401 A | 5/1988 | Walles et al. | 166/300 |
| 4,748,011 A | 5/1988 | Baize | 423/228 |
| 4,779,680 A | 10/1988 | Sydansk | 166/300 |
| 4,795,574 A | 1/1989 | Syrinek et al. | 507/238 |
| 4,817,717 A | 4/1989 | Jennings, Jr. et al. | 166/278 |
| 4,830,106 A | 5/1989 | Uhri | 166/250.1 |
| 4,846,277 A | 7/1989 | Khalil et al. | 166/280.1 |
| 4,848,468 A | 7/1989 | Hazlett et al. | 166/300 |
| 4,852,650 A | 8/1989 | Jennings, Jr. et al. | 166/250.1 |
| 4,869,322 A | 9/1989 | Vogt, Jr. et al. | 166/280.1 |
| 4,892,147 A | 1/1990 | Jennings, Jr. et al. | 166/280.2 |
| 4,926,940 A | 5/1990 | Stromswold | 166/247 |
| 4,938,286 A | 7/1990 | Jennings, Jr. | 166/280.1 |
| 4,978,512 A | 12/1990 | Dillon | 423/226 |
| 5,005,645 A | 4/1991 | Jennings, Jr. et al. | 166/280.1 |
| 5,024,276 A | 6/1991 | Borchardt | 166/308.6 |

(Continued)

FOREIGN PATENT DOCUMENTS

| | | |
|---|---|---|
| CA | 2007965 | 8/1990 |
| CA | 2125513 | 1/1995 |
| DE | 4027300 | 3/1992 |
| EP | 0730018 A1 | 9/1996 |
| GB | 775376 | 5/1957 |
| GB | 816337 A | 7/1959 |
| GB | 1073338 A | 6/1967 |
| JP | 08151422 | 6/1996 |
| JP | 10001461 | 1/1998 |
| JP | 10110115 A | 4/1998 |
| JP | 2005194148 A | 7/2005 |
| WO | WO 98/19774 | 5/1998 |
| WO | WO 98/56497 | 12/1998 |

OTHER PUBLICATIONS

U.S. Appl. No. 12/075,461, Gatlin et al.
U.S. Appl. No. 11/554,834, Venditto et al.
U.S. Appl. No. 11/765,306, Kakadjian et al.
U.S. Appl. No. 11/748,248, Thompson et al.
U.S. Appl. No. 11/736,971, Kippie et al.

(Continued)

*Primary Examiner* — Brian J Davis
(74) *Attorney, Agent, or Firm* — Robert W Strozier

(57) ABSTRACT

A novel method for producing amine-aldehyde sulfur scavenging compositions are disclosed, where the method comprises contacting an amine containing component and a aldehyde containing component in the presence of an alcohol at an amine to aldehyde ratio of between about 0.8 and 0.45 for a reaction time and at a reaction temperatures sufficient to produce an amine-aldehyde adduct product having a specific gravity between about 3% and 7% less than the specific gravity of a mixture of starting materials.

31 Claims, 18 Drawing Sheets

U.S. PATENT DOCUMENTS

| | | | | |
|---|---|---|---|---|
| 5,030,762 | A * | 7/1991 | Brake | 564/508 |
| 5,067,556 | A | 11/1991 | Fudono et al. | 62/196.4 |
| 5,074,359 | A | 12/1991 | Schmidt | 166/280.1 |
| 5,074,991 | A | 12/1991 | Weers | 208/236 |
| 5,082,579 | A | 1/1992 | Dawson | 507/211 |
| 5,106,518 | A | 4/1992 | Cooney et al. | 507/21 |
| 5,110,486 | A | 5/1992 | Manalastas et al. | 507/260 |
| 5,169,411 | A | 12/1992 | Weers | 44/421 |
| 5,224,546 | A | 7/1993 | Smith et al. | 166/300 |
| 5,228,510 | A | 7/1993 | Jennings, Jr. et al. | 166/263 |
| 5,246,073 | A | 9/1993 | Sandiford et al. | 166/295 |
| 5,259,455 | A | 11/1993 | Nimerick et al. | 166/308.5 |
| 5,330,005 | A | 7/1994 | Card et al. | 166/280.2 |
| 5,342,530 | A | 8/1994 | Aften et al. | 252/8.551 |
| 5,347,004 | A | 9/1994 | Rivers et al. | 544/180 |
| 5,363,919 | A | 11/1994 | Jennings, Jr. | 166/308.1 |
| 5,402,846 | A | 4/1995 | Jennings, Jr. et al. | 166/259 |
| 5,411,091 | A | 5/1995 | Jennings, Jr. | 166/280.1 |
| 5,424,284 | A | 6/1995 | Patel et al. | 507/129 |
| 5,439,055 | A | 8/1995 | Card et al. | 166/280.2 |
| 5,462,721 | A | 10/1995 | Pounds et al. | 423/226 |
| 5,465,792 | A | 11/1995 | Dawson et al. | 166/295 |
| 5,472,049 | A | 12/1995 | Chaffe et al. | 166/250.1 |
| 5,482,116 | A | 1/1996 | El-Rabaa et al. | 166/250.1 |
| 5,488,083 | A | 1/1996 | Kinsey, III et al. | 507/211 |
| 5,497,831 | A | 3/1996 | Hainey et al. | 166/308.1 |
| 5,501,275 | A | 3/1996 | Card et al. | 166/280.2 |
| 5,551,516 | A | 9/1996 | Norman et al. | 166/308.2 |
| 5,624,886 | A | 4/1997 | Dawson et al. | 507/217 |
| 5,635,458 | A | 6/1997 | Lee et al. | 507/240 |
| 5,649,596 | A | 7/1997 | Jones et al. | 166/300 |
| 5,669,447 | A | 9/1997 | Walker et al. | 166/300 |
| 5,674,377 | A | 10/1997 | Sullivan, III et al. | 208/208 R |
| 5,688,478 | A | 11/1997 | Pounds et al. | 423/228 |
| 5,693,837 | A | 12/1997 | Smith et al. | 556/148 |
| 5,711,396 | A | 1/1998 | Joerg et al. | 180/444 |
| 5,722,490 | A | 3/1998 | Ebinger | 166/281 |
| 5,744,024 | A | 4/1998 | Sullivan, III et al. | 208/236 |
| 5,755,286 | A | 5/1998 | Ebinger | 166/281 |
| 5,775,425 | A | 7/1998 | Weaver et al. | 166/276 |
| 5,787,986 | A | 8/1998 | Weaver et al. | 166/280.2 |
| 5,806,597 | A | 9/1998 | Tjon-Joe-Pin et al. | 166/300 |
| 5,807,812 | A | 9/1998 | Smith et al. | 507/238 |
| 5,833,000 | A | 11/1998 | Weaver et al. | 166/276 |
| 5,853,048 | A | 12/1998 | Weaver et al. | 166/279 |
| 5,871,049 | A | 2/1999 | Weaver et al. | 166/276 |
| 5,877,127 | A | 3/1999 | Card et al. | 507/273 |
| 5,908,073 | A | 6/1999 | Nguyen et al. | 166/276 |
| 5,908,814 | A | 6/1999 | Patel et al. | 507/131 |
| 5,964,295 | A | 10/1999 | Brown et al. | 166/308.5 |
| 5,979,557 | A | 11/1999 | Card et al. | 166/300 |
| 5,980,845 | A | 11/1999 | Cherry | 423/229 |
| 6,016,871 | A | 1/2000 | Burts, Jr. | 166/300 |
| 6,035,936 | A | 3/2000 | Whalen | 166/308.5 |
| 6,047,772 | A | 4/2000 | Weaver et al. | 166/276 |
| 6,054,417 | A | 4/2000 | Graham et al. | 507/238 |
| 6,059,034 | A | 5/2000 | Rickards et al. | 166/280.2 |
| 6,060,436 | A | 5/2000 | Snyder et al. | 507/266 |
| 6,069,118 | A | 5/2000 | Hinkel et al. | 507/277 |
| 6,123,394 | A | 9/2000 | Jeffrey | 299/16 |
| 6,133,205 | A | 10/2000 | Jones | 507/276 |
| 6,147,034 | A | 11/2000 | Jones et al. | 507/238 |
| 6,162,449 | A | 12/2000 | Maier et al. | 424/401 |
| 6,162,766 | A | 12/2000 | Muir et al. | 507/267 |
| 6,169,058 | B1 | 1/2001 | Le et al. | 507/222 |
| 6,228,812 | B1 | 5/2001 | Dawson et al. | 507/221 |
| 6,247,543 | B1 | 6/2001 | Patel et al. | 175/64 |
| 6,267,938 | B1 | 7/2001 | Warrender et al. | 423/226 |
| 6,283,212 | B1 | 9/2001 | Hinkel et al. | 166/279 |
| 6,291,405 | B1 | 9/2001 | Lee et al. | 507/136 |
| 6,330,916 | B1 | 12/2001 | Rickards et al. | 166/280.2 |
| 6,725,931 | B2 | 4/2004 | Nguyen et al. | 166/280.2 |
| 6,756,345 | B2 | 6/2004 | Pakulski et al. | 507/246 |
| 6,793,018 | B2 | 9/2004 | Dawson et al. | 166/300 |
| 6,832,650 | B2 | 12/2004 | Nguyen et al. | 166/279 |
| 6,875,728 | B2 | 4/2005 | Gupta et al. | 507/240 |
| 7,140,433 | B2 | 11/2006 | Gatlin et al. | 166/250.01 |
| 7,268,100 | B2 | 9/2007 | Kippie et al. | 507/244 |
| 7,350,579 | B2 | 4/2008 | Gatlin et al. | 166/308.3 |
| 2002/0049256 | A1 | 4/2002 | Bergeron, Jr. | 514/674 |
| 2002/0165308 | A1 | 11/2002 | Kinniard et al. | 524/492 |
| 2003/0220204 | A1 | 11/2003 | Baran, Jr. et al. | 507/200 |
| 2005/0045330 | A1 | 3/2005 | Nguyen et al. | 166/281 |
| 2005/0092489 | A1 | 5/2005 | Welton et al. | 166/280.2 |
| 2005/0137114 | A1 | 6/2005 | Gatlin et al. | 510/424 |
| 2005/0153846 | A1 | 7/2005 | Gatlin | 208/236 |
| 2005/0250666 | A1 | 11/2005 | Gatlin et al. | 510/492 |
| 2006/0194700 | A1 | 8/2006 | Gatlin et al. | 507/203 |
| 2007/0032693 | A1 | 2/2007 | Gatlin et al. | 507/239 |
| 2007/0129257 | A1 | 6/2007 | Kippie et al. | 507/102 |
| 2007/0131425 | A1 | 6/2007 | Gatlin et al. | 166/280.2 |
| 2007/0173413 | A1 | 7/2007 | Lukocs et al. | 507/238 |
| 2007/0173414 | A1 | 7/2007 | Wilson, Jr. | 507/131 |
| 2008/0039345 | A1 | 2/2008 | Kippie et al. | 507/213 |

OTHER PUBLICATIONS

U.S. Appl. No. 11/767,384, Sweeney et al.
U.S. Appl. No. 11/741,110, Wilson, Jr. et al.
U.S. Appl. No. 11/677,434, Wanner et al.
U.S. Appl. No. 11/736,992, Zamora et al.
U.S. Appl. No. 11/760,581, Schwartz.
U.S. Appl. No. 12/029,335, Kakadjian et al.
Sartori, F. and Savage, D.W., Sterically Hindered Amines for CO2 Removal from Gases, Ind. Eng. Chem. Fundam. 1983, 22, 239-249.
Fushslueger, U., Socher, G., Grether, H-J., Grasserbauer, M., Capillary Supercritical Fluid Chromatography/Mass Spectroscopy of Phenolic Mannich Bases with Dimethyl Ether Modified Ethane as Mobile Phase, Anal. Chem., 1999, 71, 2324-2333.
Kauffman, W.J., Observations on the Synthesis and Characterization of N,N',N"-Tris-(dimethylaminopropyly)hexahydro-s-triazine and isolable intermediates, XP009005168, 1975.
Delepine, M., Effect of Hydrogen Sulfide on Trimethyltrimethyl Triamine, Bull. Soc. Chim., 1896, 14, 889-891 (English Translation), 1896.
Delepine, M., Effect of Hydrogen Sulfide and Trimethyltrimethyl Triamine, Ann. Chim. Phys., 1896, 4, 114-133 (English Translation), 1896.
Paquin, A.M., Reaction of Primary Amines with Aliphatic Aldehydes, Chem. Ber., 1949, 82, 316-326 (English Translation), 1949.
Castillo, M., Avila, Y.S., Rodrigues, R.E., Viloria, A., H2S Liquid Scavengers, Their Corrosivity Properites and the Compatibility with Other Down Stream Processes, Corrosion 2000, paper 00491, 2000.

* cited by examiner

ALDEHYDE-AMINE FORMULATIONS AND METHOD FOR MAKING AND USING SAME

BACKGROUND OF THE INVENTION

1. Field of the Invention

Embodiments of this invention relates to a novel and dependable process for preparing effective aldehyde-amine products, e.g., certain embodiments being formaldehyde-amine products, usable as noxious sulfur scavengers.

More particularly, embodiments of this invention relates to a novel and dependable process for preparing effective aldehyde-amine products, e.g., certain embodiments being formaldehyde-amine products, usable as noxious sulfur scavengers, where the process efficiently produces aldehyde-amine adduct products that do not form solids or gels upon exposure to fluids or gases containing noxious sulfur species, in the case of formaldehyde-amine adducts, are substantially or completely formaldehyde free (no detectable formaldehyde), are cost effective, and are non-foaming. The lack of solids reduces the plugging of production equipment or the plugging of pipe lines, which is not only undesirable, but can also be hazardous.

2. Description of the Related Art

In prior art, stepwise addition of formaldehyde to desired moles of amine has been taught in U.S. Pat. No. 5,030,762 and references cited therein. Sterically hindered amines have also been employed in U.S. Pat. No. 4,112,052. Aldehyde adducts of polymers like polyacylamide are described in U.S. Pat. No. 4,230,608; polyimines in U.S. Pat. No. 5,128,049; direct use of trithianes are additional examples of alternative teachings available in prior art.

Even though many aldehyde-amine and formaldehyde-amine adducts have been disclosed, many of these adducts form solids or gels, especially when exposed to fluids or gases containing noxious sulfur containing species, contain free formaldehyde or generate free formaldehyde upon exposure to fluids or gases containing noxious sulfur containing species, when formaldehyde is the aldehyde, form foams, and are cost ineffective. Thus, there is a need in the art for an effective process for preparing commercially effective aldehyde-amine adduct products that are formaldehyde free, when formaldehyde is the aldehyde, efficient, non-foaming, and non-solid forming and/or gel forming.

SUMMARY OF THE INVENTION

Embodiments of this invention provides a new process for the preparation of aldehyde-amine adduct products that is reproducible, producing a unique and effective aldehyde-amine products. The method utilizes an amine to aldehyde ratio of approximately 1:2 (or 0.5) reacted in the presence of an alcohol at a temperature and for a time sufficient to produce an aldehyde-amine product having a specific gravity so that the product has a scavenging activity greater than a scavenging activity of a composition prepared using a higher or lower amine to formaldehyde ratio. In certain embodiment, the ratio is between about 0.8 and about 0.45. In certain embodiments, the scavenging activity at least one fold higher than a product prepared with a higher or lower amine to aldehyde ratio.

Embodiments of this invention provides a new process for the preparation of formaldehyde-amine adduct products that is reproducible, producing a unique and effective formylated product. The method utilizes an amine to formaldehyde ratio of approximately 1:2 in the presence of an alcohol at a temperature and for a time sufficient to achieve a desired specific gravity, where the formylated products have scavenging activities nearly threefold higher than compositions prepared using a higher amine to formaldehyde ratio. i.e., ratios greater than about 0.5. In certain embodiment, the ratio is between about 0.8 and about 0.45.

Embodiments of this invention provides a formaldehyde-amine adduct or formylated product prepared by the reaction of an amine and formaldehyde at a ratio of about 1:2 in the presence of an alcohol at a temperature and for a time sufficient to achieve a desired specific gravity. In certain embodiment, the ratio is between about 0.8 and about 0.45.

Embodiments of this invention provides a method for reducing noxious sulfur containing fluids or gases comprising adding an effective aldehyde-amine adduct product, certain embodiments a formaldehyde-amine adduct product, prepared by the reaction of an amine and formaldehyde at a ratio of about 1:2 in the presence of an alcohol at a temperature and for a time sufficient to produce a product having a specific gravity and characterized by having a higher scavenging activity compared to a product produced with a higher or lower amine to aldehyde ratio to the fluid or gases, where the effective amount is sufficient to reduce the amount of noxious sulfur containing components in the fluid or gas. In certain embodiment, the ratio is between about 0.8 and about 0.45. Usage is dependent on operation conditions (e.g., crude composition, level of $H_2S$, temperature, flow rate or the like); however, about 3.5 moles of the gas is completely removed per liter of the adduct under laboratory screening conditions.

BRIEF DESCRIPTION OF THE DRAWINGS

The invention can be better understood with reference to the following detailed description together with the appended illustrative drawings in which like elements are numbered the same.

DETAILED DESCRIPTION OF THE INVENTION

Figure 1A:
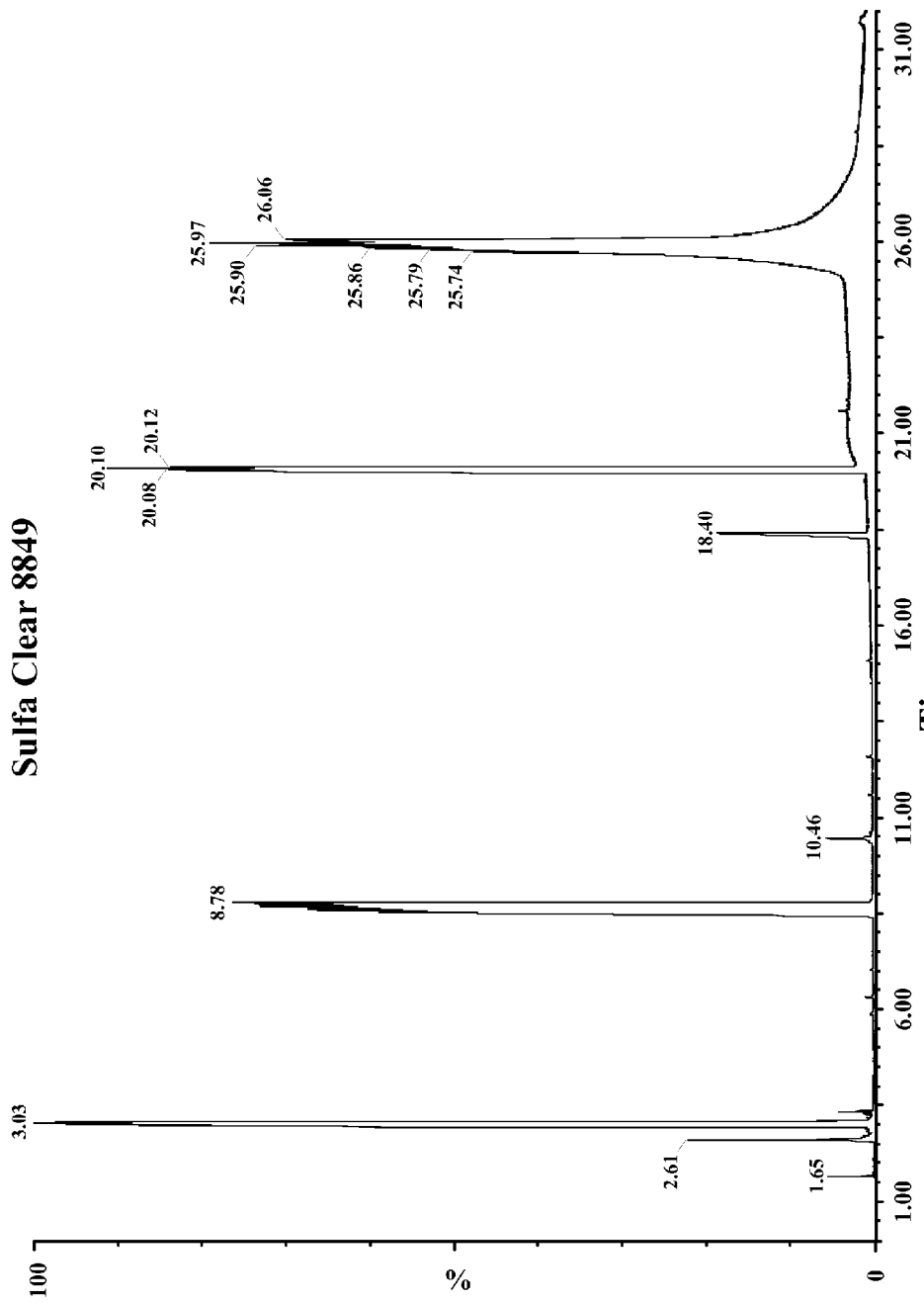
FIGS. 1A-F depict GC/MS chromatograms of formylated product prepared at different mole ratios and different temperatures.
Figure 1B:
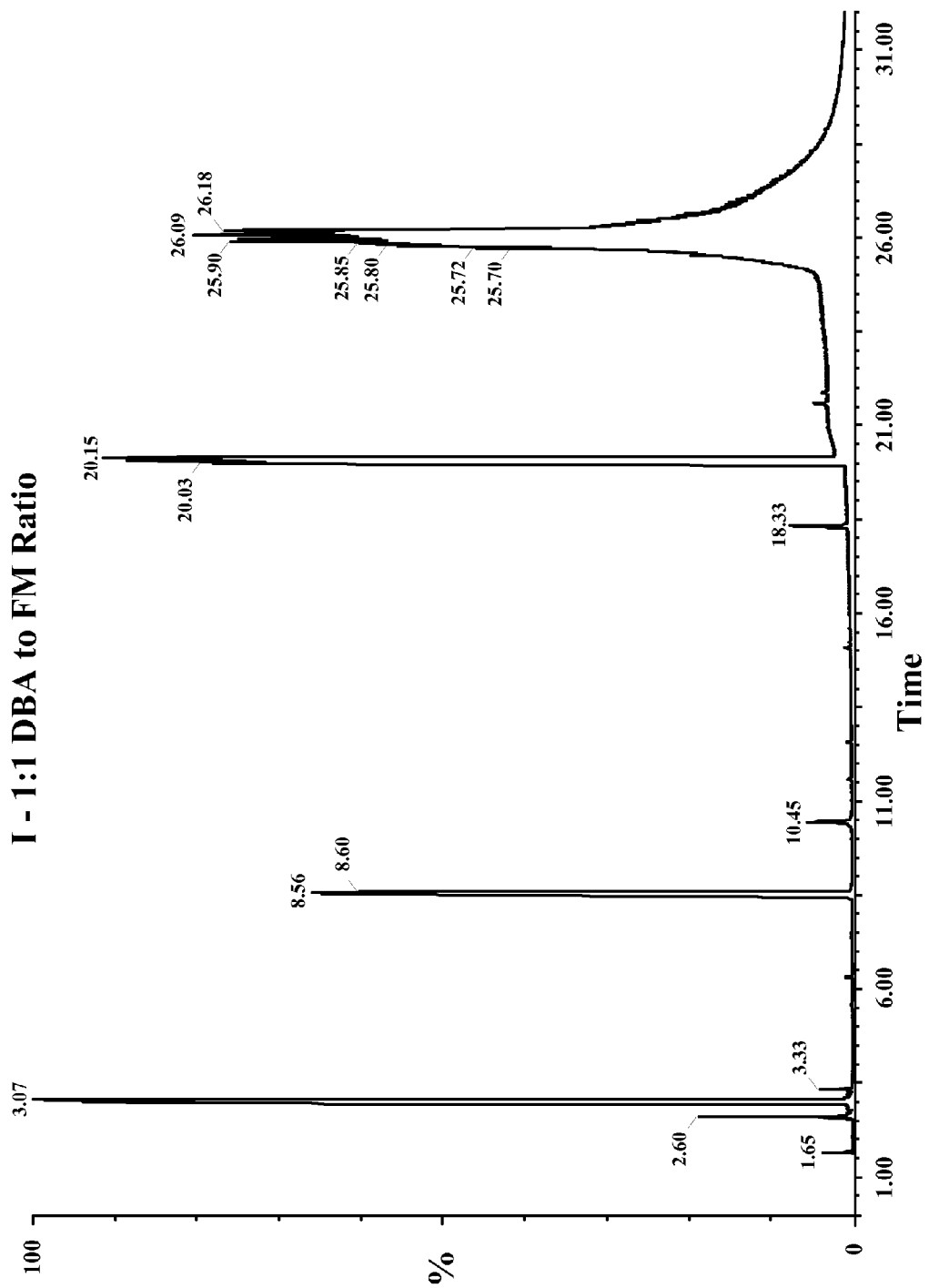
Figure 1C:
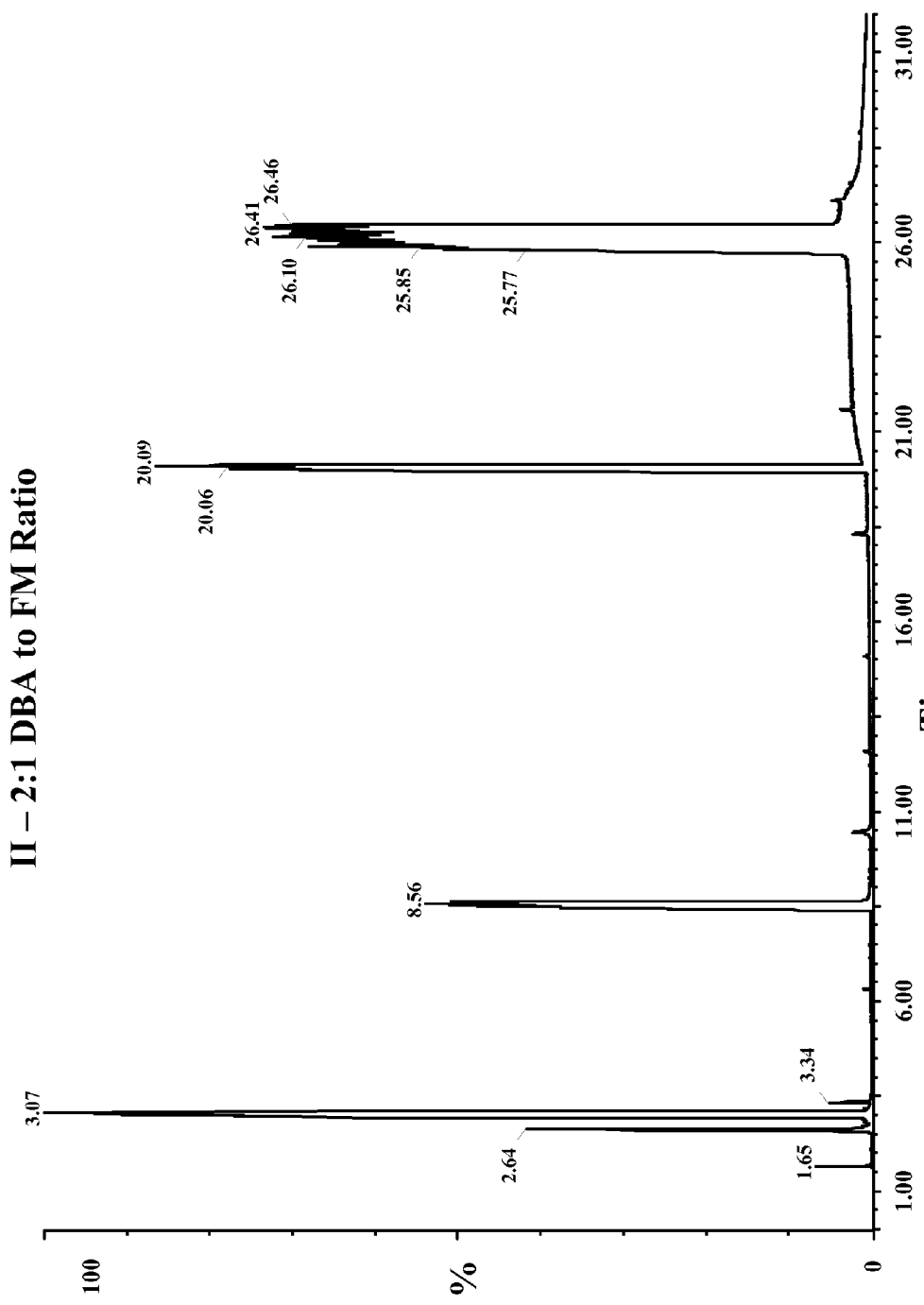
Figure 1D:
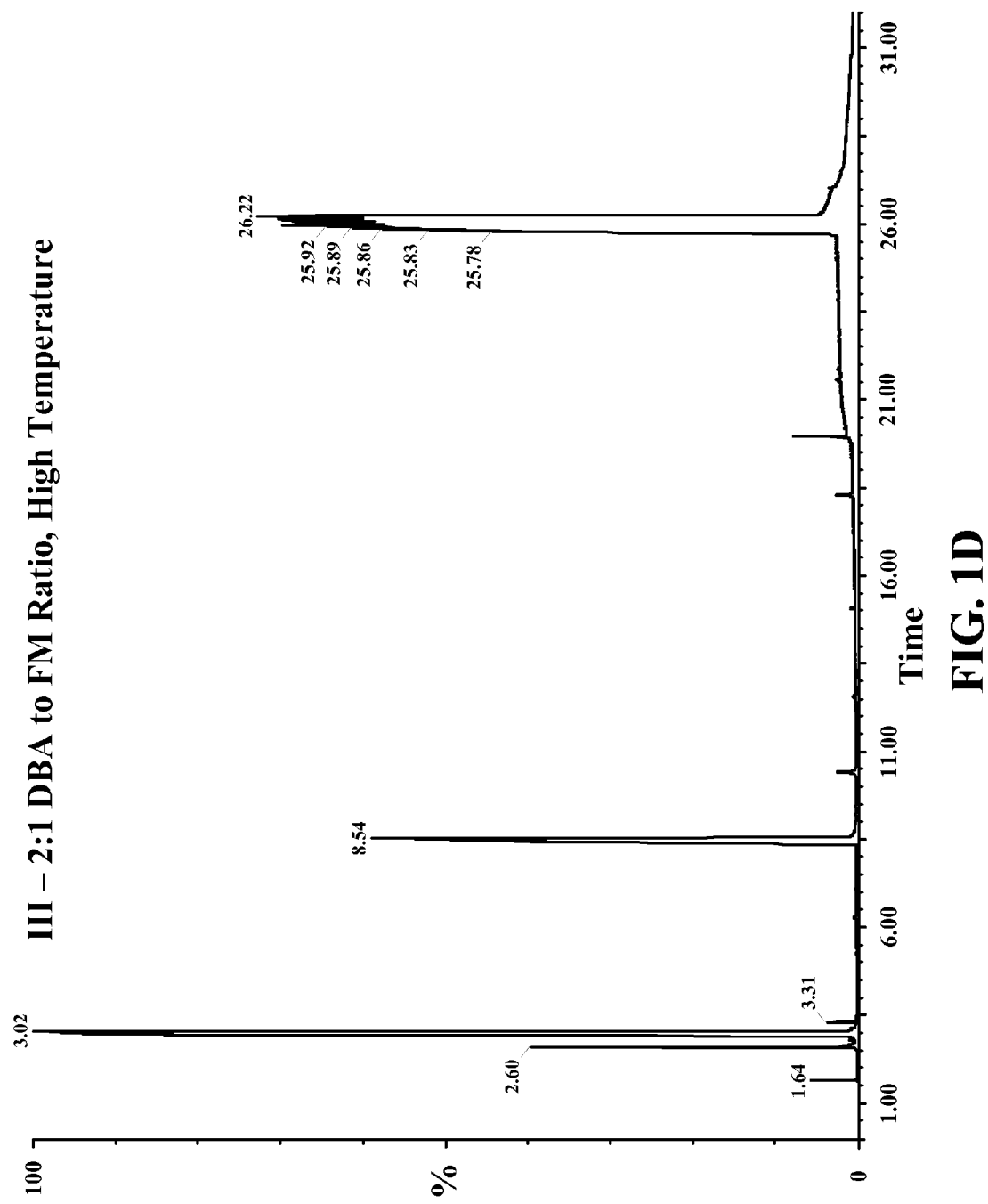

The inventors have found that formulations of aldehyde-amine adducts can be prepared with optimal sour gas scavenging capacity. The inventors have also found a reproducible process for manufacturing the formulations. The inventors have also found that specific gravity can be used to control the manufacturing process. The inventors have also found that the addition of alcohols during the amine-formaldehyde reaction mixtures give rise to alcoholic adducts which cooperate in the scavenging propensity of the formulations of this invention. The products are characterized in that the specific gravity of the product be between 3% and 7% less than the specific gravity of the true mixture of starting materials and that the reaction time is less than about 12 hours. In certain embodiments, the products are characterized in that the specific gravity of the product be between 4% and 6% less than the specific gravity of the true mixture starting materials. Additionally, the adducts are characterized by having a number of peaks in their GC/MS chromatogram between about 16 minutes and about 31 minutes. In other embodiments, the adducts are characterized by a sharp peak and trailing shoulder in its GC/MS chromatogram appearing at between about 21 minutes and about 31 minutes for a dibutyl amine/formaldehyde product. The process efficiently produces aldehyde-amine adduct products that do not form solids or gels upon exposure to fluids or gases containing noxious sulfur species, in the case of formaldehyde-amine adducts, are substantially or completely formaldehyde free (no detectable formaldehyde), are cost effective, and are non-foaming. The lack of solids reduces the plugging of production equipment or the plugging of pipe lines, which is not only undesirable, but can also be hazardous. The term substantially means that the amount of detectable formaldehyde is below the acceptable levels set by governmental agencies.

A new process for the preparation of aldehyde-amine adduct products has been developed. The process is reproducible, producing a unique and effective formulation. Surprisingly, an amine to aldehyde ratio of approximately 1:2 was established as optimal. In prior art teaching, alcohol has been added as a reaction solvent and/or to help stabilize reaction product. However, alcohol present during the amine-aldehyde reaction was found to result in the formation of highly effective adduct formulations. Scavenging capacity test results were surprisingly impressive with activities in certain embodiments nearly threefold those of prior art or current commercial formulations. Thus, adduct products produced with greater amine to aldehyde ratios >0.5 or lower amine to aldehyde ratios <0.5 give inferior products. In certain embodiment, the inventors have found amine to aldehyde ratios between about 0.8 and about 0.45. In other embodiments, the inventors have found amine to aldehyde ratios between about 0.75 and 0.45. The process efficiently produces aldehyde-amine adduct products that do not form solids or gels upon exposure to fluids or gases containing noxious sulfur species, in the case of formaldehyde-amine adducts, are substantially or completely formaldehyde free (no detectable formaldehyde), are cost effective, and are non-foaming. The lack of solids reduces the plugging of production equipment or the plugging of pipe lines, which is not only undesirable, but can also be hazardous. In certain embodiments, the reaction time is between about 5 and about 12 hours. In other embodiments, the reaction time is between about 8 and about 12 hours. In other embodiments, the reaction time is between about 9 and about 12 hours. In other embodiments, the reaction time is between about 9.5 and 12 hours.

Embodiments of this invention broadly relates to a new process for the preparation of formaldehyde-amine adduct products that is reproducible, producing a unique and effective formulation, using an amine to aldehyde (e.g., formaldehyde) ratio of approximately 1:2 in the presence of an alcohol at a temperature and for a time sufficient to achieve a desired specific gravity, where the formulation has a higher scavenging activity than compositions prepared with higher or lower ratios. In certain embodiments, the formulations of this invention can be nearly threefold higher than compositions prepared using a higher or lower amine to formaldehyde ratios. In certain embodiment, the inventors have found amine to aldehyde ratios between about 0.8 and about 0.45. In other embodiments, the inventors have found amine to aldehyde ratios between about 0.75 and 0.45. The process efficiently produces aldehyde-amine adduct products that do not form solids or gels upon exposure to fluids or gases containing noxious sulfur species, in the case of formaldehyde-amine adducts, are substantially or completely formaldehyde free (no detectable formaldehyde), are cost effective, and are non-foaming.

Embodiments of this invention also broadly relates to a formaldehyde-amine adduct product prepared by the reaction of an amine and formaldehyde at a ratio of about 1:2 in the presence of an alcohol at a temperature and for a time sufficient to achieve a desired specific gravity, where the formulation has a higher scavenging activity than compositions prepared with higher or lower ratios. In certain embodiment, the inventors have found amine to aldehyde ratios between about 0.8 and about 0.45. In other embodiments, the inventors have found amine to aldehyde ratios between about 0.75 and 0.45. The aldehyde-amine adduct products do not form solids or gels upon exposure to fluids or gases containing noxious sulfur species, in the case of formaldehyde-amine adducts, are substantially or completely formaldehyde free (no detectable formaldehyde), are cost effective, and are non-foaming.

Embodiments of this invention also broadly relates to a method for reducing noxious sulfur containing of fluids or gases comprising adding an effective a formaldehyde-amine adduct product prepared by the reaction of an amine and formaldehyde at a ratio of about 1:2 in the presence of an alcohol at a temperature and for a time sufficient to achieve a desired specific gravity, where the formulation has a higher scavenging activity than compositions prepared with higher or lower ratios, to the fluid or gases, where the effective amount is sufficient to reduce the amount of noxious sulfur containing components in the fluid or gas. In certain embodiment, the inventors have found amine to aldehyde ratios between about 0.8 and about 0.45. In other embodiments, the inventors have found amine to aldehyde ratios between about 0.75 and 0.45. The aldehyde-amine adduct products do not form solids or gels upon exposure to fluids or gases containing noxious sulfur species, in the case of formaldehyde-amine adducts, are substantially or completely formaldehyde free (no detectable formaldehyde), are cost effective, and are non-foaming.

Result & Discussion
I. Chemistry
I.1. Reagents

In the current practice, for an amine: formaldehyde adduct product, an amine to formaldehyde molar equivalent ratio of 1:1.33 (0.75:1) is used to prepare a formylated N,N-dibutylamine (DBA) product. This product is currently sold as Sulfa Clear 8849 or WFT 9809 available from Weatherford International of Houston, Tex., USA. Table 1 tabulates data on two current formulations of this formylated N,N-dibutylamine (DBA) product. Paraformaldehyde is the formaldehyde (FM) source used in these formylation process examples.

TABLE 1

Reagents and Equivalents

| Description | Quantity (lb) | FW | Moles | Mol Eq. | Molar Ratio |
|---|---|---|---|---|---|
| Formula 1 | | | | | |
| N,N-Dibutyl amine | 68.02 | 129 | 0.527 | 0.383 | 0.751 |
| Paraformaldehyde | 21.06 | 30 | 0.702 | 0.510 | 1 |
| n-Butyl alcohol | 10.92 | 74 | 0.148 | 0.107 | |
| | 100 | | 1.377 | 1.000 | |
| Formula 2 | | | | | |
| N,N-Dibutyl amine, bulk | 76.36 | 129 | 0.592 | | 0.751 |
| Paraformaldehyde | 23.64 | 30 | 0.788 | | 1 |
| | 100 | | 1.380 | | |
| n-Butyl alcohol | 12.26 | 74 | 0.166 | | |
| | 112.26 | | 1.546 | | |

Starting with the current reagent formula as set forth in Table 1, the inventors varied the DBA to FM ratio and varied the reaction temperature in the presence or absence of n-butanol (BT) to determine whether a repeatable method and a reproducible product could be designed to overcome the problems associated with the current product and its manufacturing.

I.1.a. N,N-Dibutylamine to Paraformaldehyde Ratio

N,N-Dibutylamine (DBA) to paraformaldehyde (FM) molar ratios of 1:1, 1:2, 1:2.5, 1:3,2:1, 1.5:2 were studied in preparations of formylated adducts and tested for $H_2S$ scavenging capacity. The scavenging capacity for each formulation (in terms of breakthrough time in minutes) of resultant reaction products were tested and the results are tabulated in Table2 including initial observations.

TABLE 2

Formylation with Various Molar Ratios of Reagents

| [DBA][1] Mol | [FM][2] Mol | Effectiveness, Min[3] | Comment |
|---|---|---|---|
| Control | | 57 | Commercial Product. |
| 2 | 1 | 40 | |
| 1 | 1 | 75 | |
| 1 | 2 | 112 | Efficiency is 100%. Standard formulation |
| 1 | 2 | 86 | n-Butanol added ONLY after formylation |
| 1 | 2.5 | Not Applicable | Significant amount of unreacted FM seen |
| 1 | 3 | Not Applicable | Significant amount of unreacted FM seen |
| 2 | 1 | 52 | Reacted at reflux, HT (high temperature) |

[1][DBA]: Concentration of N,N-dibutylamine, DBA.
[2][FM]: Concentration of formaldehyde, FM.
[3]Corrected From the results tabulated in Table 2, a DBA to FM ratio of 1:2 produced a formulation with the highest effective $H_2S$ scavenging capacity. Next, process conditions were optimized to reproducibly produce products with the same and/or better scavenging capacity or effectiveness than found in current products or products prepared with different amine-aldehyde mole ratios.

I.1.b. Reaction with and without n-Butanol

The inventors also found that adding an alcohol such as n-butanol at the onset of reaction rather than after the reaction produced products having scavenging capacities higher than products prepared in the absence of alcohol. In the former, a breakthrough time of 112 minutes was achieved; whereas in the latter, a breakthrough time of 86 minutes was achieved as tabulated in Table 2. In addition to acting as an adduct stabilizing solvent, in prior art, addition of alcohol is known to yield ether-amine adducts. However, the beneficial effect of such amine derivatives has not been taught to the best of our knowledge. Therefore, in certain embodiments, an alcohol such as n-butanol is present during the reaction to yield adducts that are believed to include amine-aldehyde (e.g., amine-formaldehyde) adducts and amine-aldehyde-alcohol (e.g., amine-formaldehyde-alcohol) adducts.

I.2. Temperature

The amine-aldehyde reaction is known to be temperature dependent, but is not the only variable to effect resulting product composition and properties. For instance, choice of catalyst was also found to have an effect on product composition and properties. Catalysts can be acids or bases. The inventors have found that the nature and concentration of catalyst have been explored in preparing target molecules or fortuitously found to produce unique derivatives. Linear or cyclic (Calixarenes) products of phenol-formaldehyde reactions are representative of cases well know in the art. As depicted in Table 2, the inventors have found that derivatives formed in high temperature reactions (e.g., 4 h reflux) is more active (52 min) than derivatives formed at lower temperature (e.g., 40 min, ~86° C.). Still, reaction temperature is beneficial to some point. However, when the temperature is raised too high, derivatives had poorer performance.

I.3. Suitable Reagents

Suitable sources of formaldehyde include, without limitation, 37% formaldehyde in water, paraformaldehyde, formaldehyde donors, or mixtures or combinations thereof.

Suitable alcohols include, without limitation, linear or branched alcohols having from one to 20 carbon atoms, where one or more carbon atoms can be replaced by one or more hetero atoms selected from the group consisting of boron, nitrogen, oxygen, phosphorus, sulfur or mixture or combinations thereof and where one or more of the hydrogen atoms can be replaced by one or more single valence atoms selected from the group consisting of fluorine, chlorine, bromine, iodine or mixtures or combinations thereof. The oxygen replacements can be in the form of ether moieties; the nitrogen replacements can be in the form of tertiary amine or amide moieties.

Suitable amine for use in this invention include, without limitation, primary amines, secondary amines or mixtures or combinations thereof. Exemplary amines include, without limitation, $R^1R^2NH$, where $R^1$ and $R^2$ are hydrogen atoms or carbyl groups, where $R^1$ and $R^2$ cannot both be hydrogen. The carbyl groups are groups having between 1 and 20 carbon atoms where one or more carbon atoms can be replaced by one or more hetero atoms selected from the group consisting of boron, nitrogen, oxygen, phosphorus, sulfur or mixture or combinations thereof and where one or more of the hydrogen atoms can be replaced by one or more single valence atoms selected from the group consisting of fluorine, chlorine, bromine, iodine or mixtures or combinations thereof. The oxygen replacements can be in the form of ether moieties; the nitrogen replacements can be in the form of tertiary amine or amide moieties.

Noxious sulfur species include, without limitation, all sulfur containing compounds that cause gas or oil to be sour. Exemplary examples including hydrogen sulfide ($H_2S$), low molecular weight thiols (RSH, where R is a carbyl groups having between 1 and about 6 carbon atoms or equivalents thereof). Sulfur scavengers react with these sulfur species to form high molecular weight sulfur containing compounds having reduced volatility and reduced harmful properties toward metals and other downstream equipment, e.g., pipelines, separators, strippers, refinery equipment, etc.

II. Process Development

Understanding reaction progress and when to halt reaction is of considerable economic importance and the ability to reproducibly manufacture a product is equally important. To gain insight into the progression of formylation of N,N-dibutylamine (DBA), a representative example of an amine-aldehyde adduct sulfur scavenger, the process was monitored and a quality control method was developed on the basis of changes observed in physical properties during the reaction.

II.1. Reaction Progress

Upon the realization that different formylated products are obtainable overtime and at different reaction temperatures, attempts were made to monitor reaction progress using chromatography. A GC/MS method was chosen for the analysis of liquid formylation products. Referring now to FIGS. 1A-F, GC/MS chromatograms of: (a) a commercial sample designated Sulfa Clear 8849 FIG. 1A, (b) a 1 to 1 amine to formaldehyde ratio product designated I FIG. 1B, (c) a 2 to 1 amine to formaldehyde ratio product designated II FIG. 1C, (d) a 2 to 1 amine to formaldehyde ratio product prepared at high temperature designated III FIG. 1D, (e) a 1 to 2 amine to formaldehyde product, the standard formulation, designated IV FIG. 1E, and (f) a 1 to 2 amine to formaldehyde ratio product prepared without n-butanol designated V FIG. 1F. These product formulations are included in Table 2. It is apparent from the chromatograms that the product distribution changes with changes in reactant ratio, with changes in temperature and in the presence or absence of alcohol.

Using the chromatogram as a reference, aliquots of various reactions at scheduled times were probed. Consequently, optimum temperature, reaction time and target formulation were established for a 1 to 2 amine to formaldehyde product. Referring to FIGS. 2A-D, GC/MS chromatograms of: (a) the standard formulation run for 7.5 hours FIG. 2A, (b) the standard formulation run for 9.5 hours FIG. 2B, (c) the standard formulation run for 11.5 hours FIG. 2C, and (d) the standard formulation run for 13.5 hours FIG. 2D. The time chromatograms show that at time of about 11.5 hours appears optimal. The range for optimal product is fairly tightly established between about 9.5 hours and about 12 hours, with times of 13.5 hours being detrimental to final product properties.

Figure 2A:
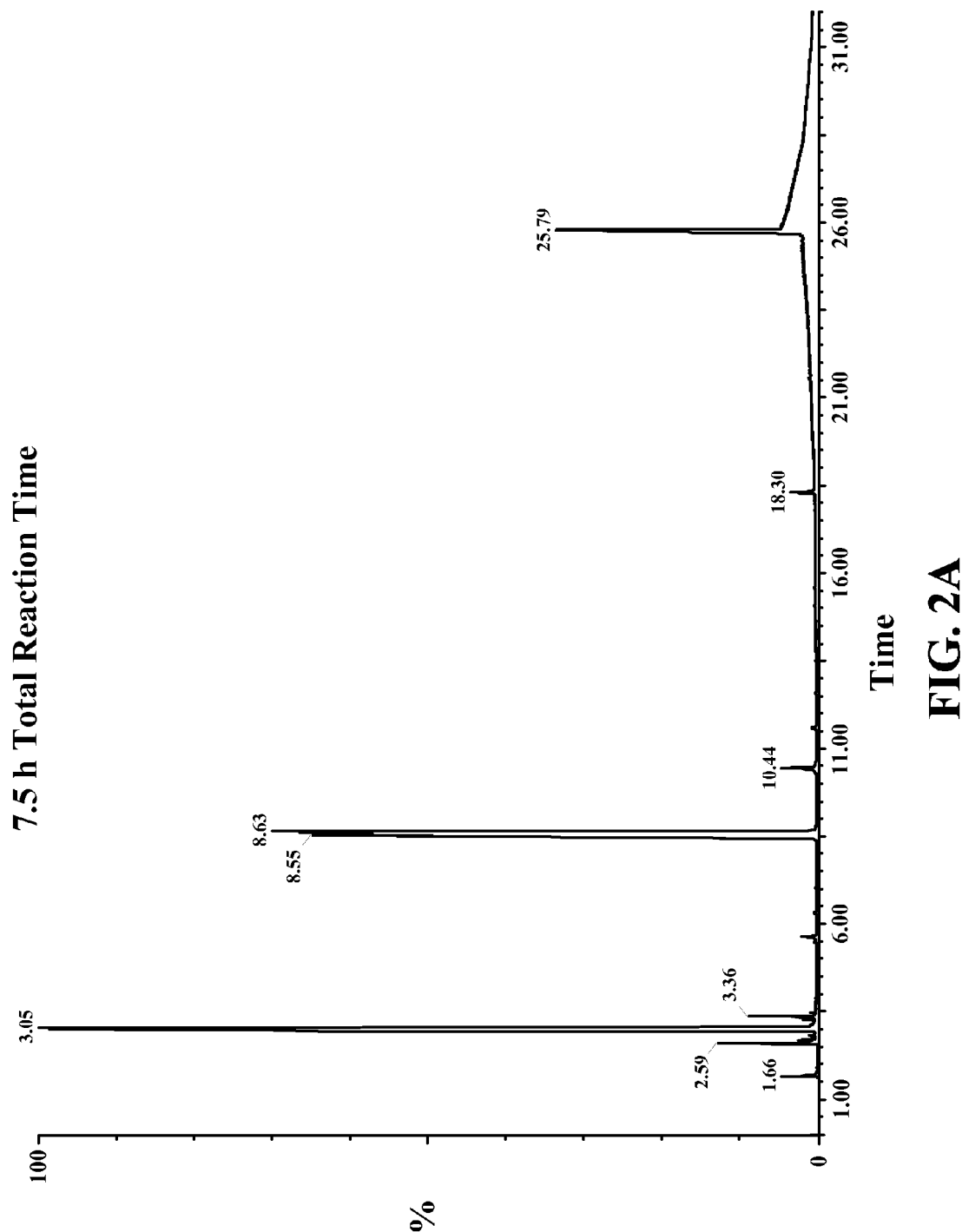
FIGS. 2A-D depict GC/MS chromatograms of formylated product prepared at different reaction times.
Figure 2B:
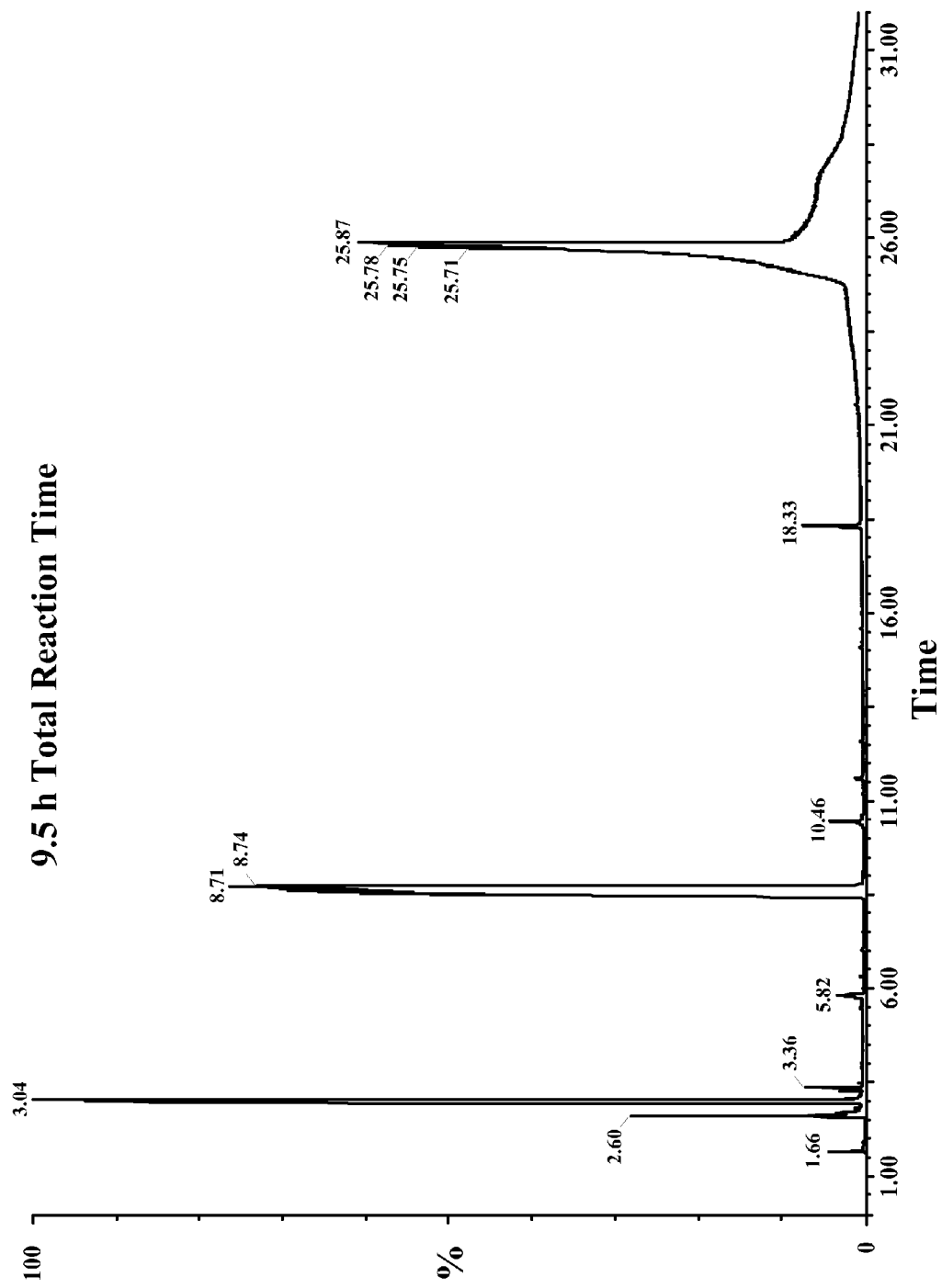
Figure 2C:
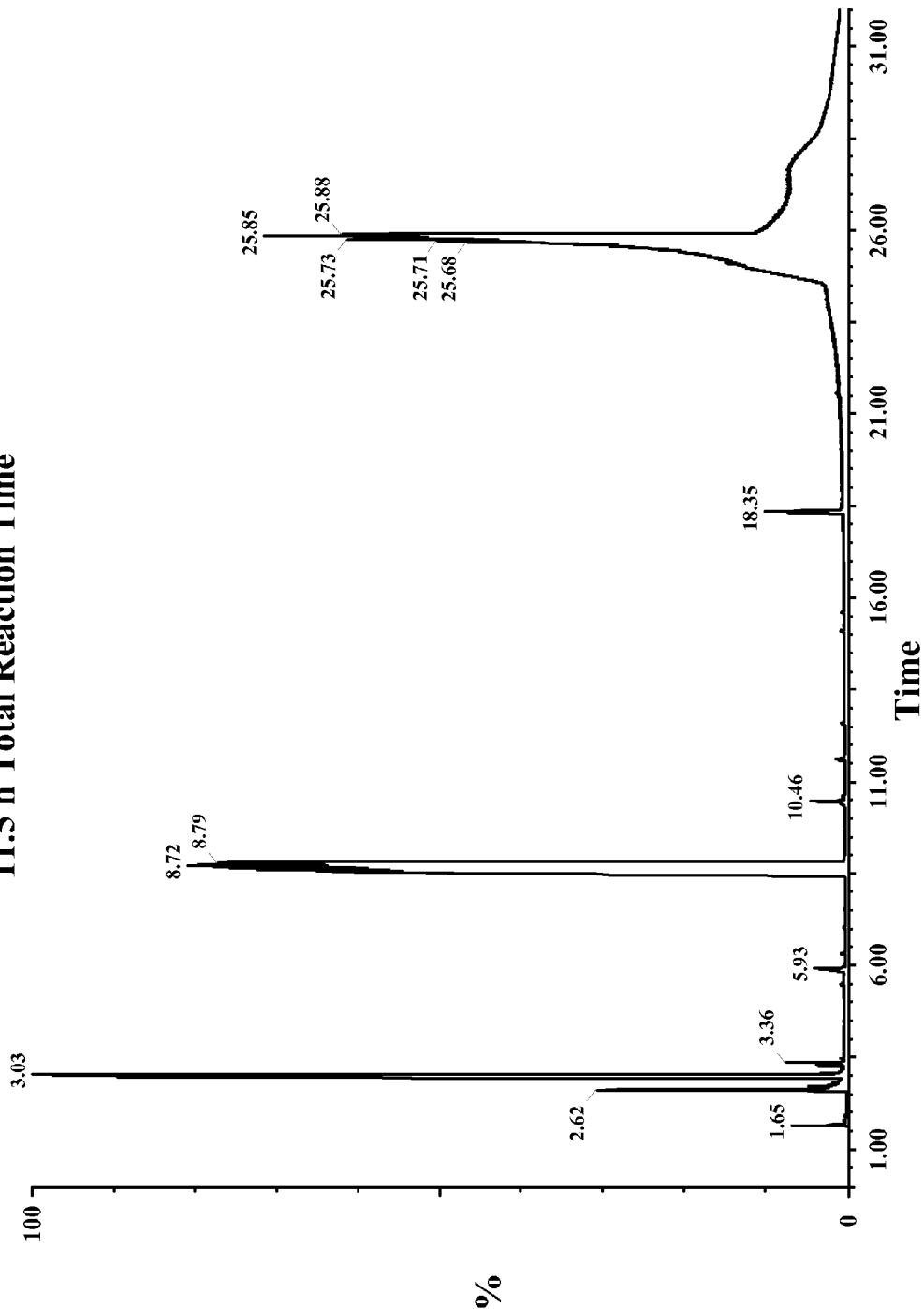
Figure 2D:
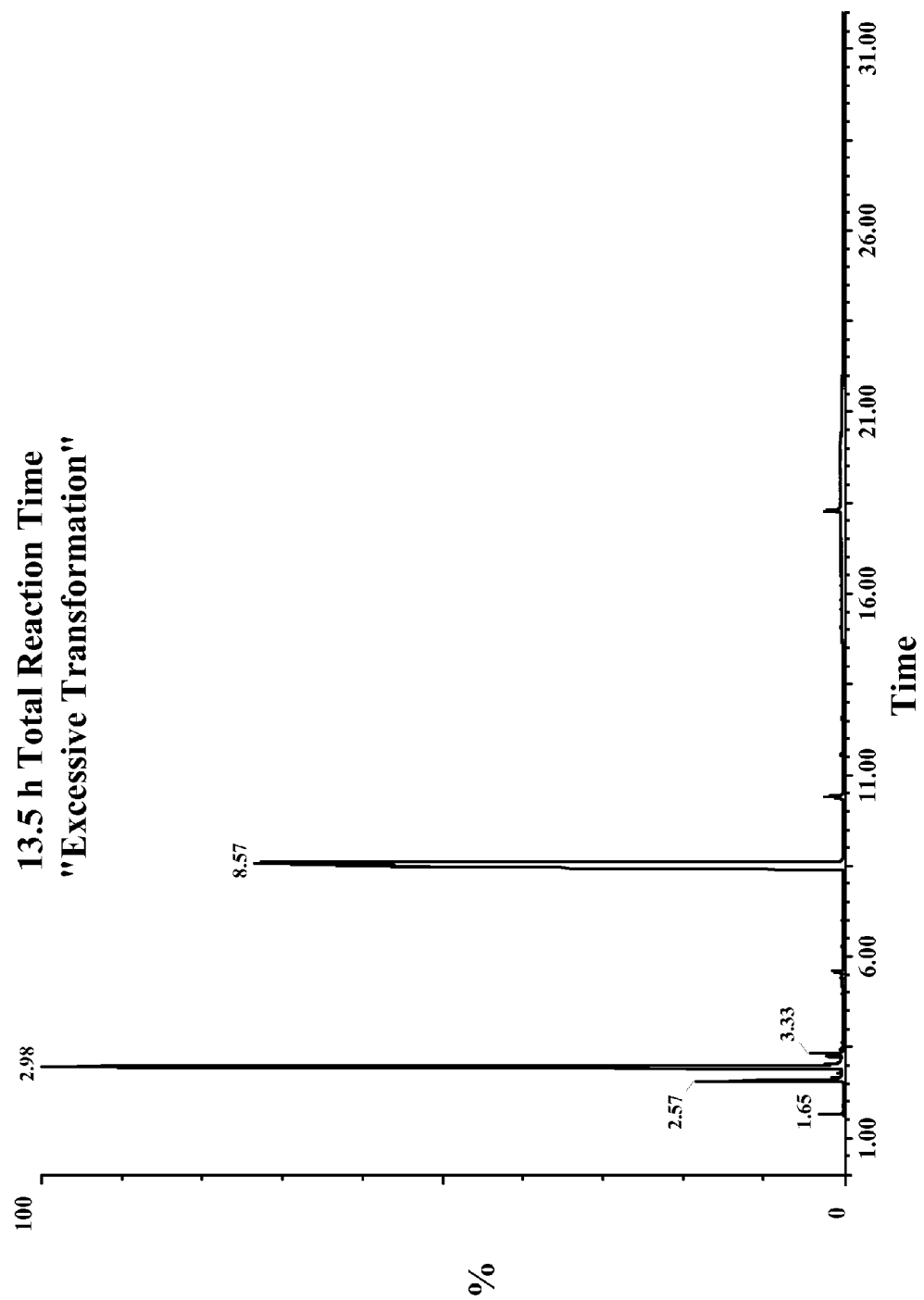

Albeit, running a GC/MS in the course of a reaction process for the prime purpose of proper reaction termination point is risky. The risk here is associated with transformation of a desirable formulation into an undesirable formulation (referred to as "excessive transformation" as shown in FIG. 2A).

II.2. Quality Control

In order to minimize the risk of losing a reaction batch because of "excessive reaction" (FIG. 2A), a shorter and dependable alternative means of monitoring reaction progress including quality of resultant formylated product was developed to replace or supplement the use of GC/MS. Specific gravities of the products tabulated in Table 2 were found to be appreciably different. Specific gravity (SG) appeared to be product specific regardless of reaction time and to some extent regardless of average reaction temperature.

II.3. Specific Gravity

Specific gravity was tested as a product quality control metric by measuring the specific gravity of aliquots withdrawn from the reaction at time intervals between 30 min or 1 h after all the paraformaldehyde had dissolved or the optimal reaction temperature of between about 86° C. and about 96° C. (about 170° F. and about 200° F.) was attained. The resulting measured specific gravities are tabulated in Table 3.

TABLE 3

Formulations and Corresponding Specific Gravity Values

| [DBA]¹ Mol | [FM]² Mol | Sample ID | Effectiveness, Min | Specific Gravity |
|---|---|---|---|---|
| Control | | Sulfa Clear 8849 | 57 | 0.806 |
| 1 | 1 | I | 75 | 0.824 |
| 2 | 1 | II | 40 | 0.806 |
| 2 | 1 | III | 86 | 0.796 |
| 1 | 2 | IV | 112 | 0.829 |

Figure 1E:
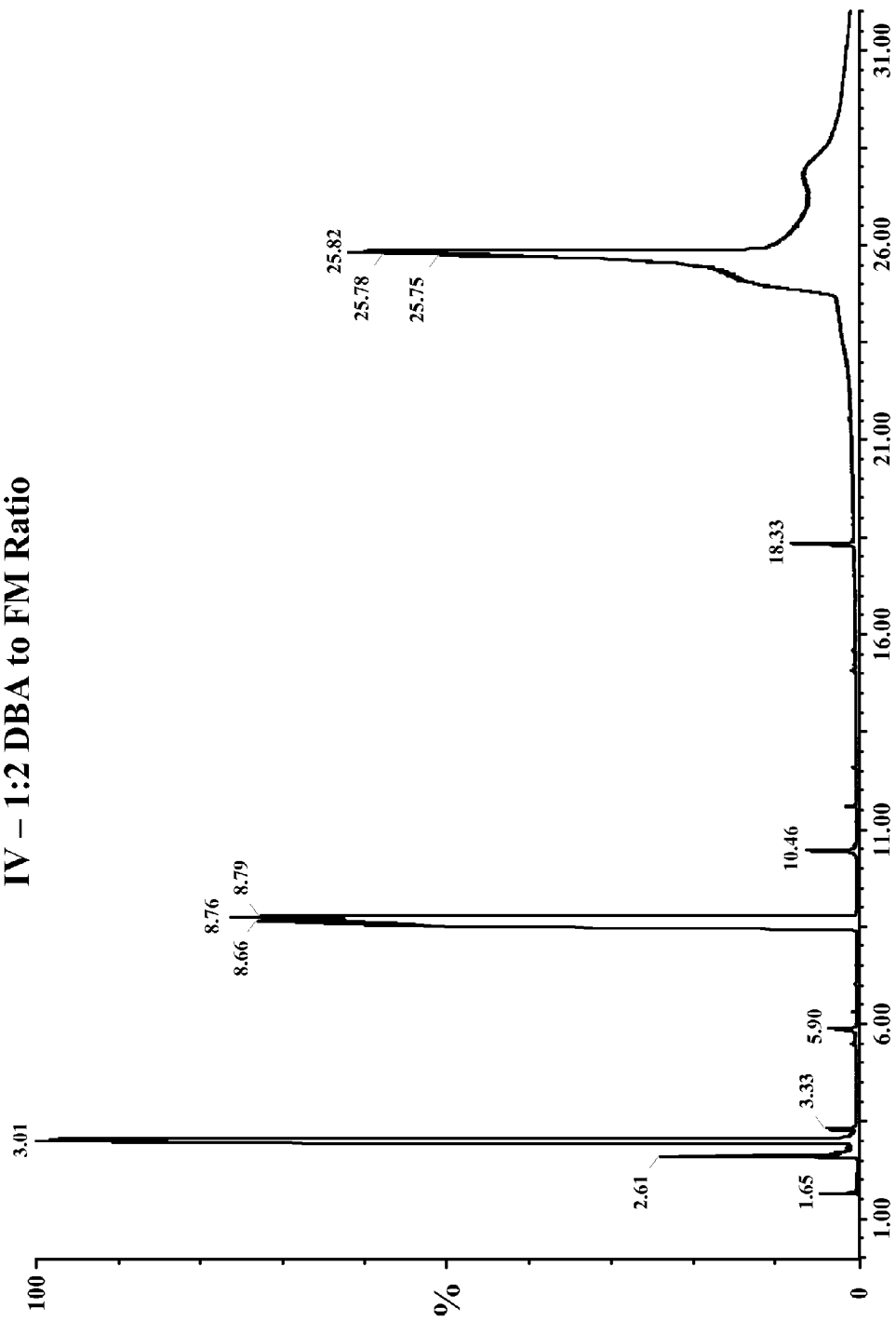
Figure 1F:
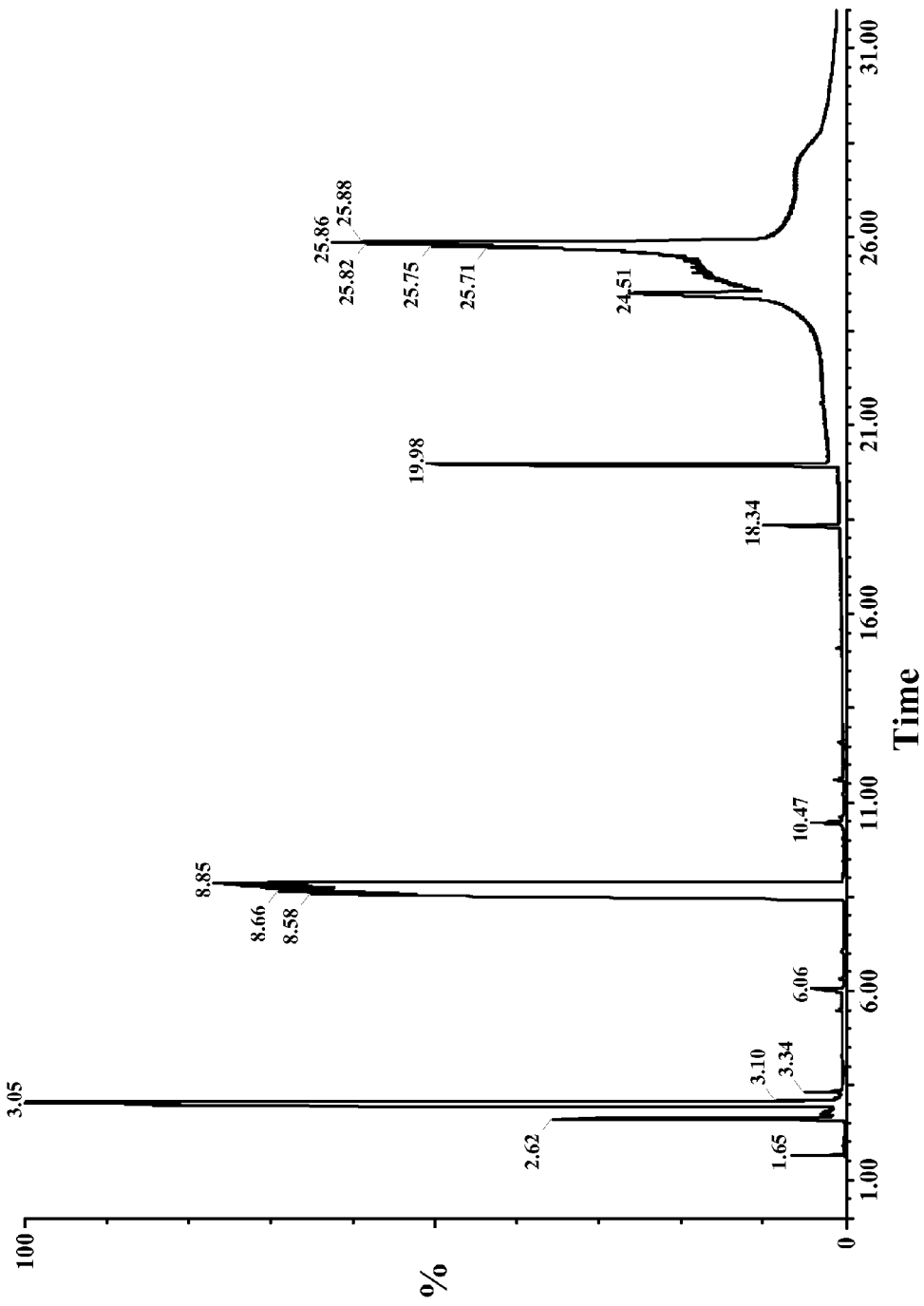
Figure 3:
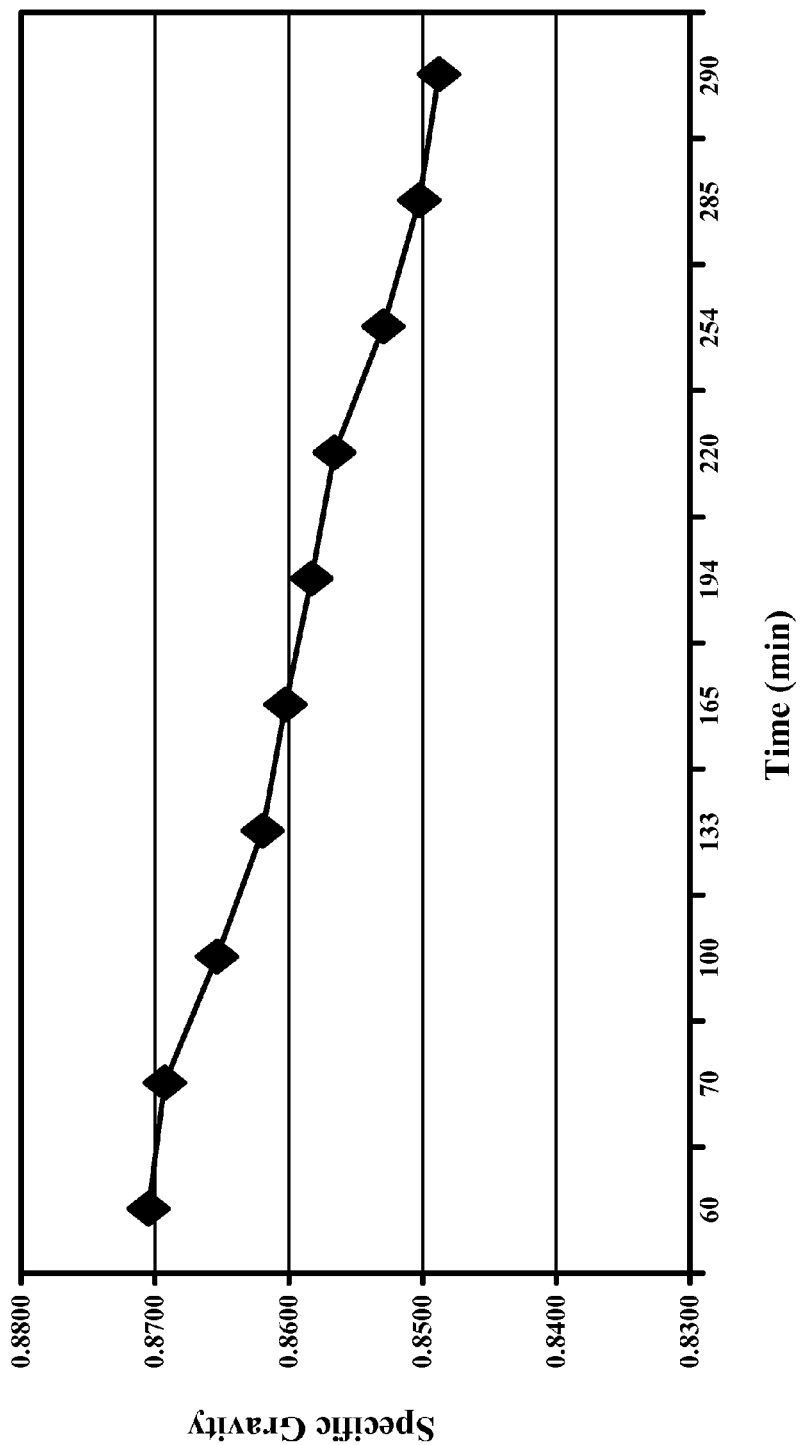
FIG. 3 depicts a plot of specific gravity versus reaction time.
Figure 4A:
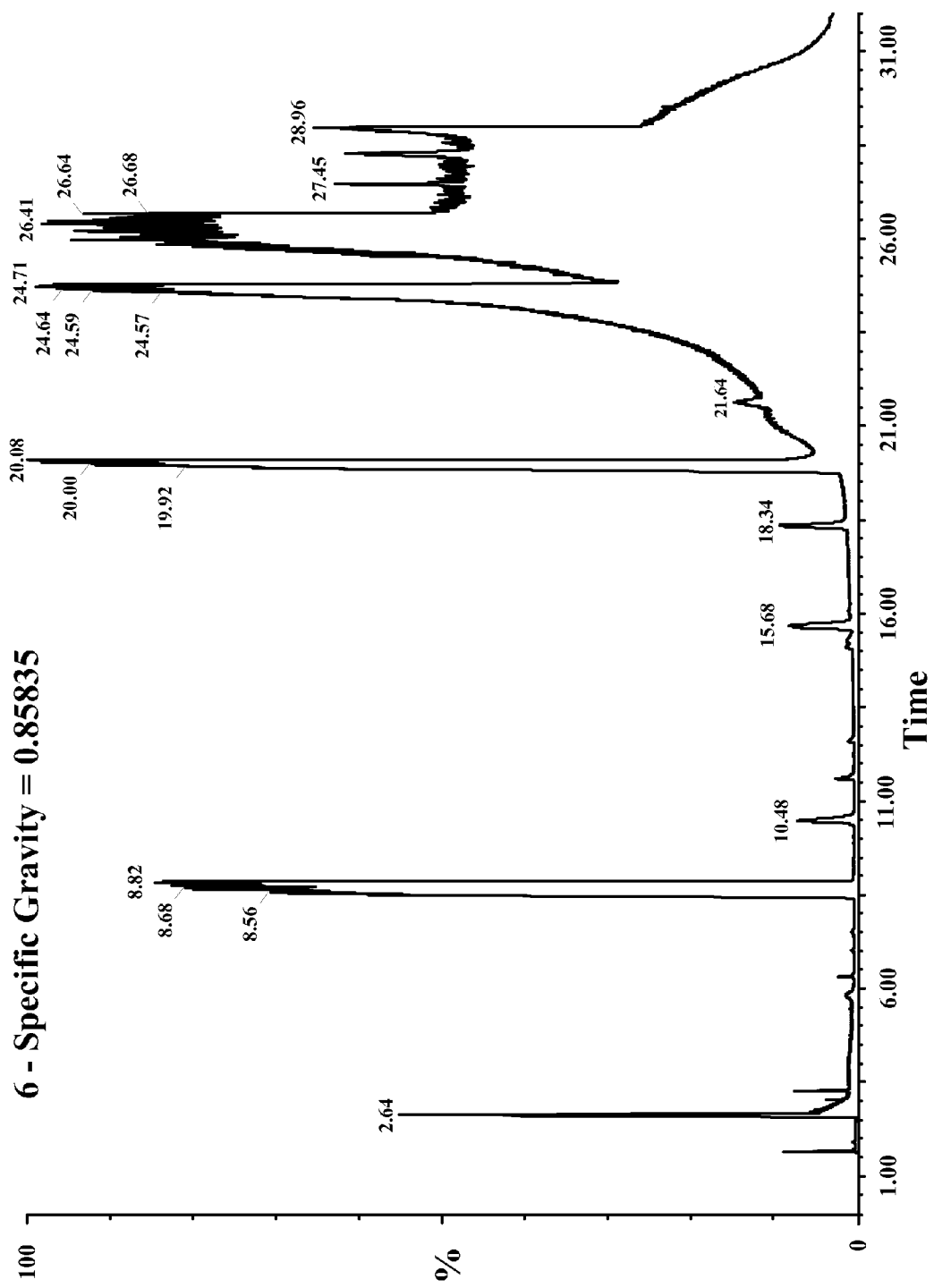
FIGS. 4A-F depict GC/MS chromatograms of aliquots of the formylated product of FIG. 3 taken at specific reaction times.
Figure 4B:
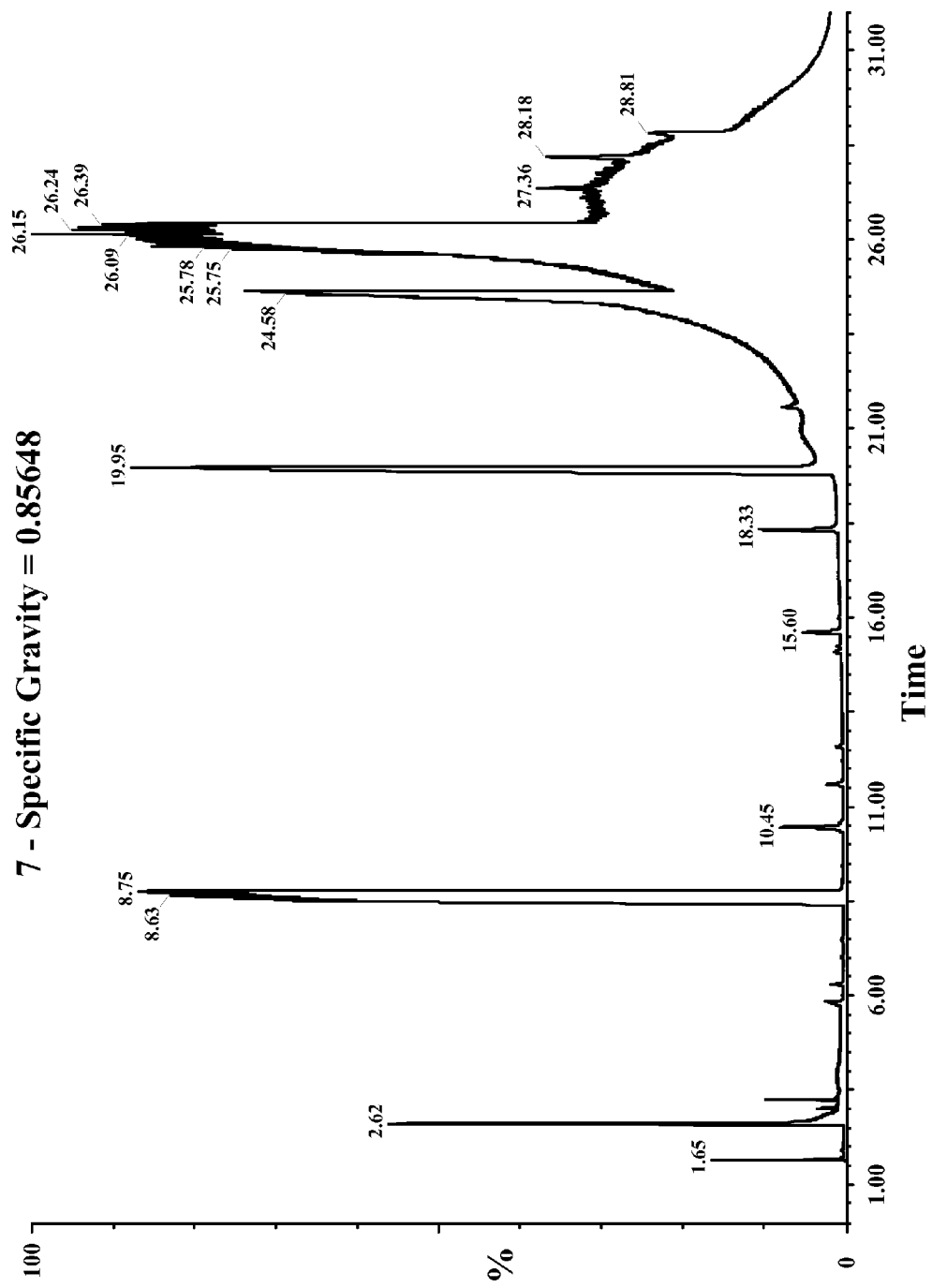
Figure 4C:
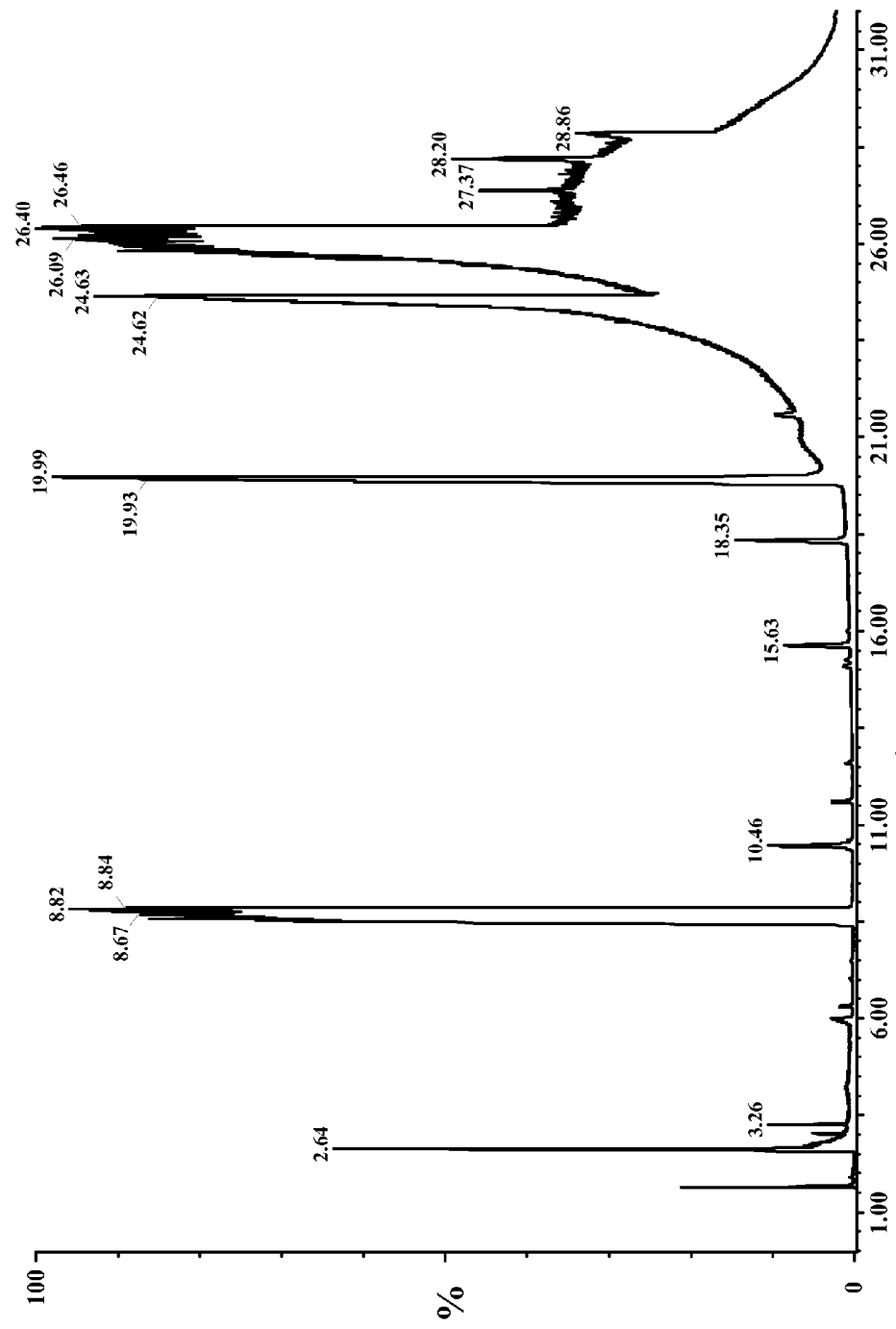
Figure 4D:
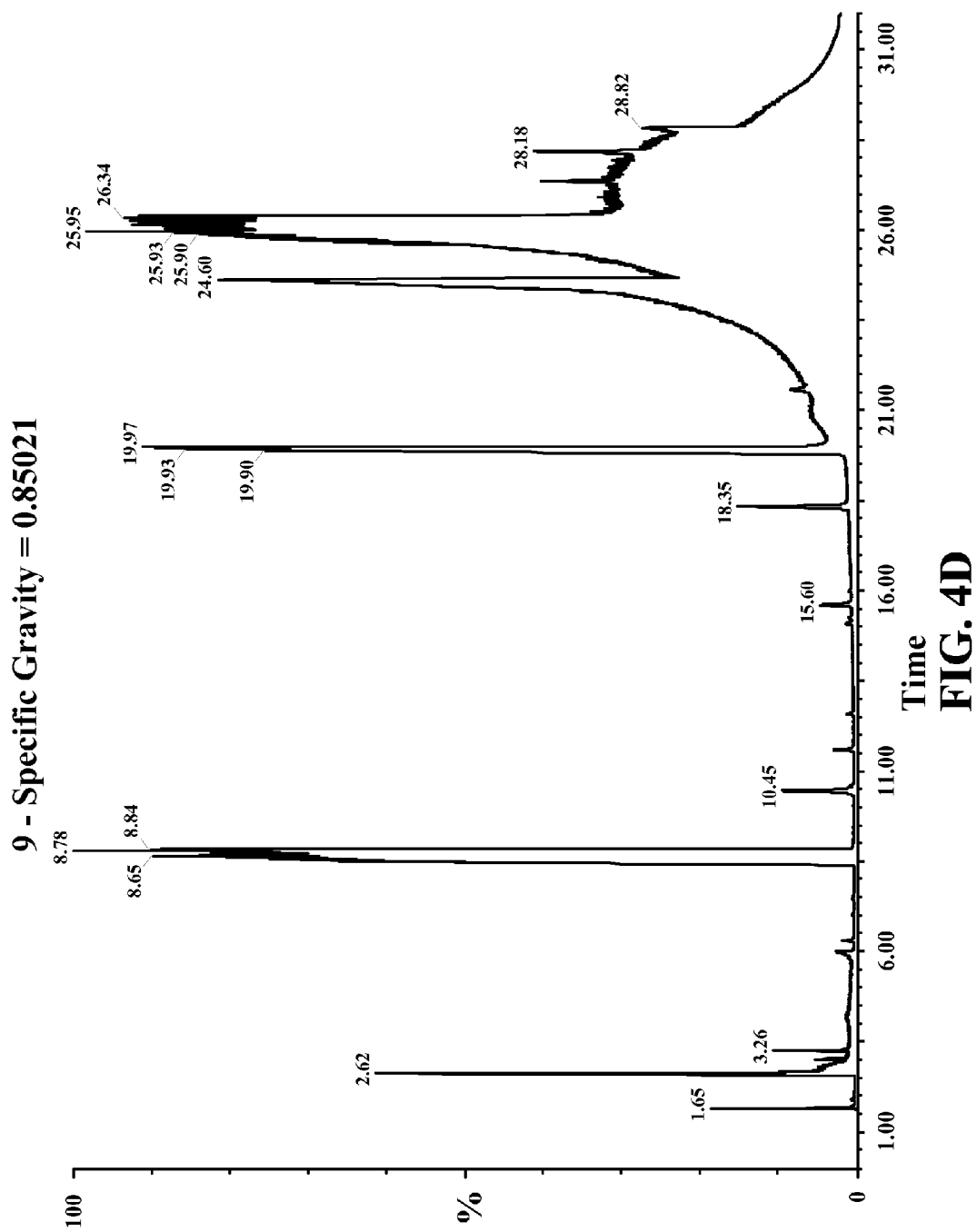
Figure 4E:
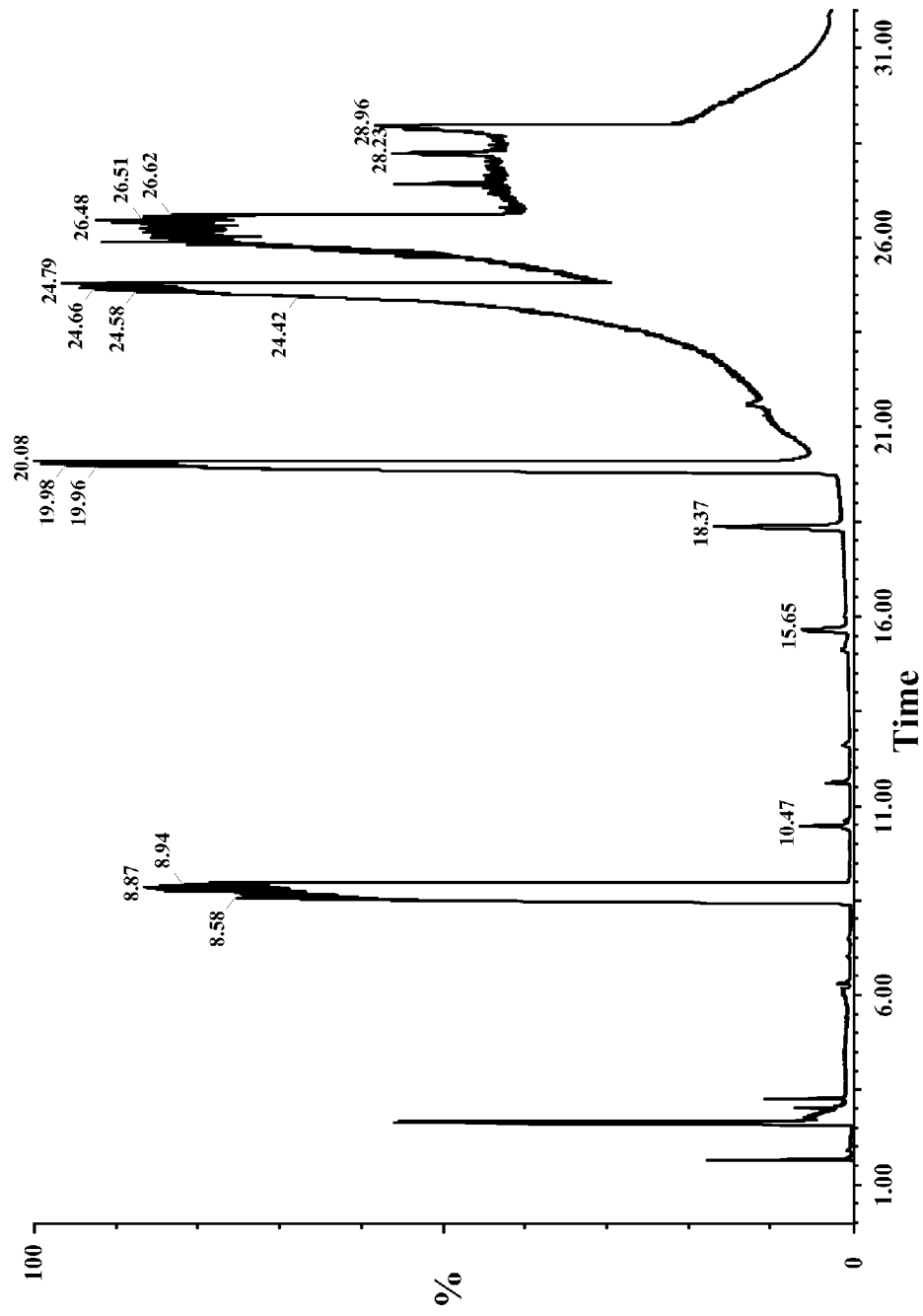
Figure 4F:
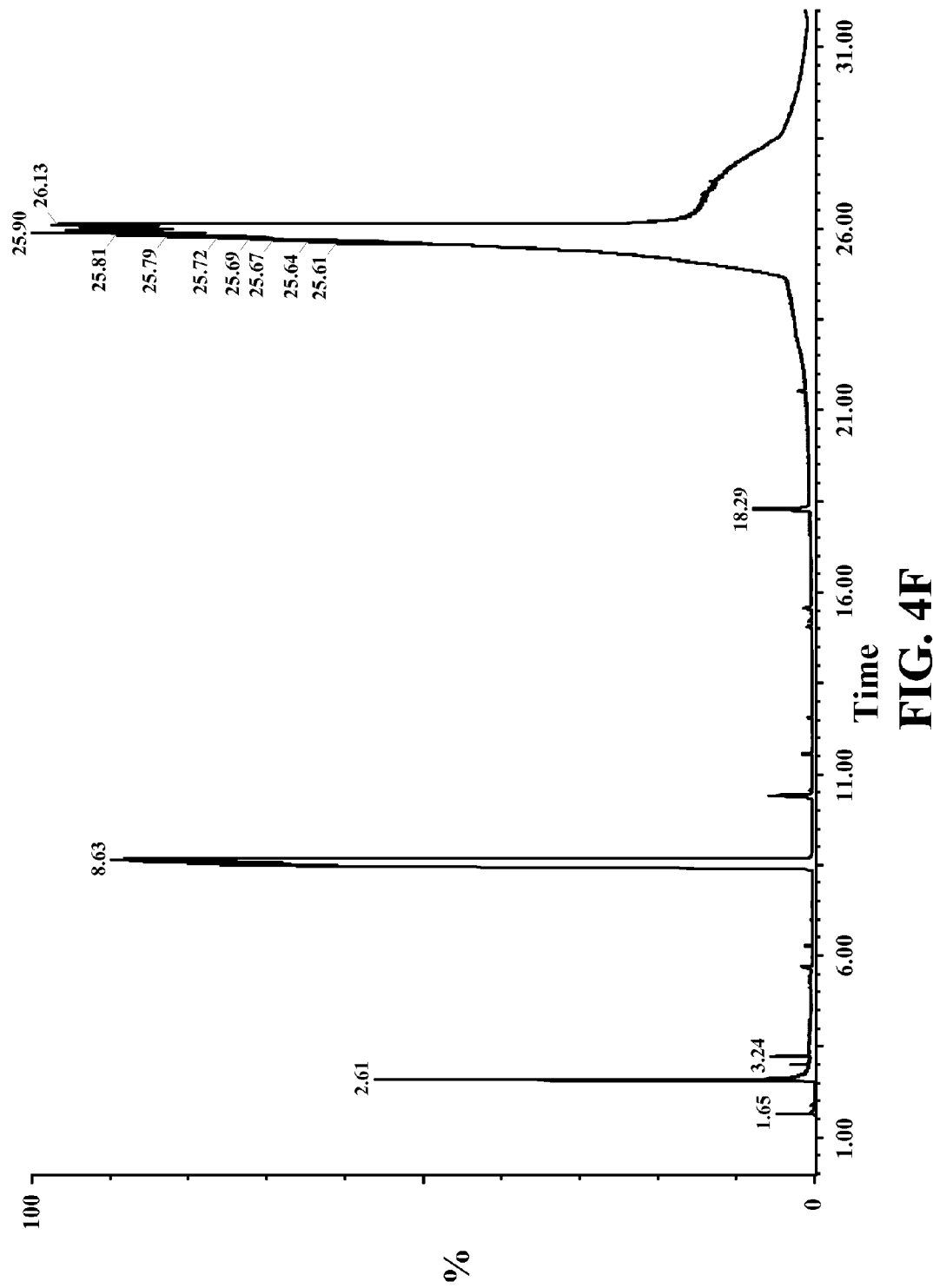

¹[DBA]: Concentration of N,N-Dibutylamine, DBA.
²[FM]: Concentration of Formaldehyde, FM.
³Corrected Then, a reaction of the 1:2 ratio formaldehyde product was carried out, with aliquots of the reaction at different reaction times were withdrawn and their corresponding specific gravity (SG) and GC/MS chromatograms were recorded. The specific gravity data are tabulated in Table 4 and graphed in FIG. 3. Representative chromatograms for selected entries of the aliquots tabulated in Table 4 are shown in FIGS. 4A-F as compared to the standard product IV as shown in FIG. 1E.

TABLE 4

Specific Gravity versus Reaction Time

| Sample ID | Time (min) | Specific Gravity | SG/QC |
|---|---|---|---|
| 1 | 60 | 0.87049 | 0.8705 |
| 2 | 70 | 0.86929 | 0.8693 |
| 3 | 100 | 0.86546 | 0.8655 |
| 4 | 133 | 0.86207 | 0.8621 |
| 5 | 165 | 0.86026 | 0.8603 |
| 6 | 194 | 0.85835 (FIG. 4A) | 0.8584 |
| 7 | 220 | 0.85648 (FIG. 4B) | 0.8565 |
| 8 | 254 | 0.85283 (FIG. 4C) | 0.8528 |
| 9 | 285 | 0.85021 (FIG. 4D) | 0.8502 |
| 10 | 290 | 0.84885 (FIG. 4E) | 0.8489 |
| 11 | | 0.84993 (FIG. 4F) | 0.8489 |
| IV | | 0.8290 (FIG. 1E) | 0.8290 |

SG and sulfur scavenging effectiveness data for pilot plant runs and the timed run 1 compared to the top performing formulation VI and the standard formulation IV are tabulated in Table 5). The data demonstrated conclusively that specific gravity is a dependable method for following the reaction and for quality control of resultant product.

In light of the 100% efficiency of the standard formula, IV, a SG of between 0.8280 and 0.8600 is a metric for producing product embodiments with generally optimized scavenging activities. The inventors have found that SG is an ideal primary QC standard or measure, while in certain embodiments, MS/GC represents a secondary QC measure, where the desirable products show a primary sharp peak with a trailing shoulder at about 26 minutes in the MS/CG chromatogram.

TABLE 5

Specific Gravities and Corresponding H₂S Scavenging Capacity of Formulations

| Sample ID | Effectiveness, Min¹ | Specific Gravity |
|---|---|---|
| IV | 112 | 0.8290 |
| 11 | 137 | 0.8488 |
| VI | 147 | 0.8477 |
| SA08060810 | 127 | 0.8456 |
| SA08060811 | 135 | 0.8432 |

¹Corrected

IV. Pilot Plant Glass Reactor Unit Process

Figure 5:
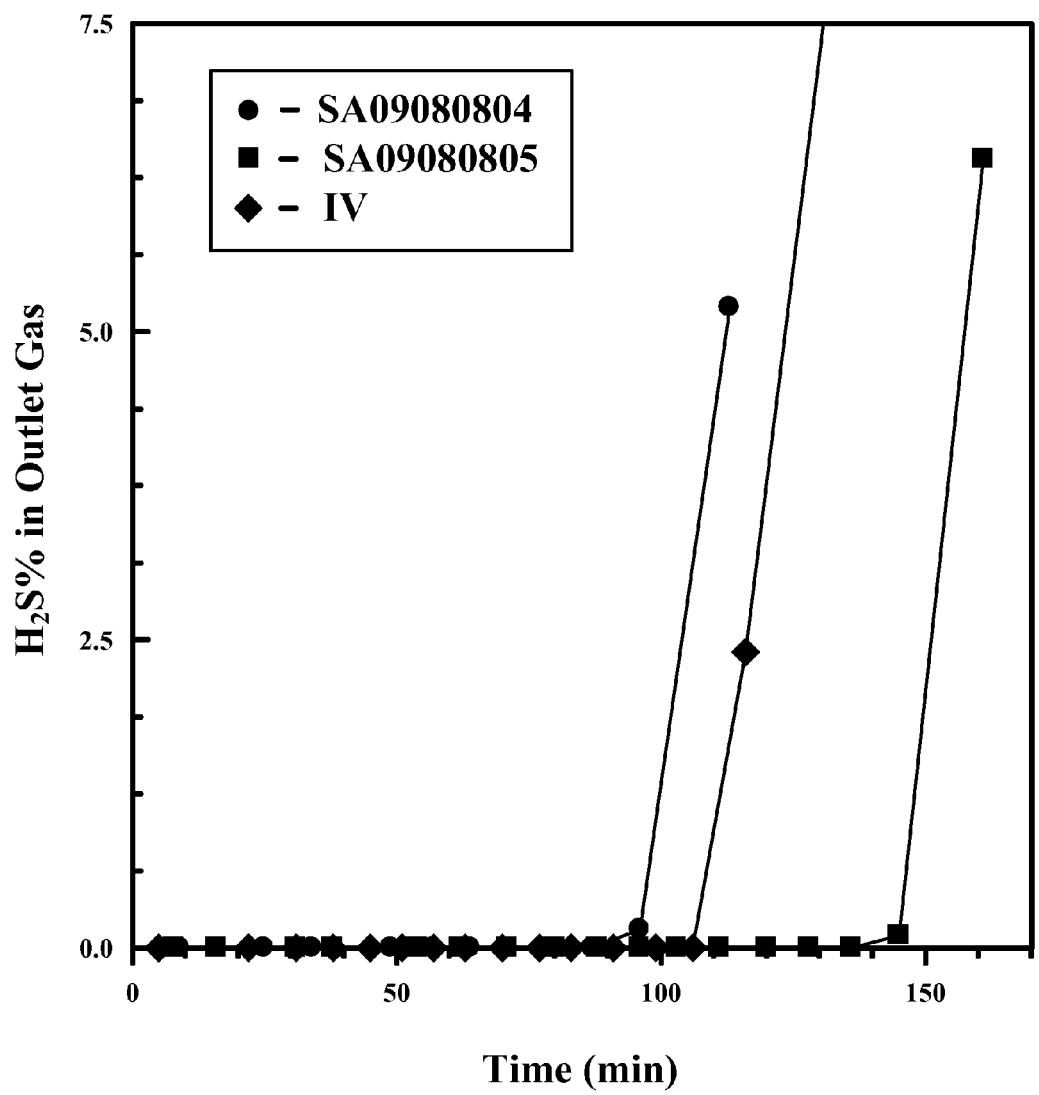
FIG. 5 depicts a plot of sulfur ($H_2S$) scavenging versus time.

To a 55 gallon reactor, add paraformaldehyde (76.71 lb), N,N-dibutyl amine (166 lb) and n-butanol (29.74 lb). Upon agitation, initial reaction temperature reached about 65° C. Then, reaction temperature was gradually raised to 90° C. and maintained at a temperature between about 90° C. and about 92° C. with intermittent cooling/heating as needed. Pressure was also maintained under 50 psi by venting reactor to scrubber. Samples were collected at 30 min interval and corresponding specific gravity (SG) and density determined. Reaction was stopped when SG of adduct measured 0.8422 and 1.3 times more effective scavenging capacity than the standard, IV (see lot samples SA09080804 and SA09080805 in FIG. 5). Of importance is the ability of the adducts to completely remove the noxious gas as evidenced by the flat trend exhibited by the samples as depicted in FIG. 5 and yet with neither the formation of solids nor foams.

All references cited herein are incorporated by reference. Although the invention has been disclosed with reference to its preferred embodiments, from reading this description those of skill in the art may appreciate changes and modification that may be made which do not depart from the scope and spirit of the invention as described above and claimed hereafter.

We claim:

1. A method for preparing amine-aldehyde adduct products comprising:

contacting an amine containing component and an aldehyde containing component in the presence of an alcohol at an amine to aldehyde ratio of between about 0.8 and 0.45 for a reaction time and at a reaction temperatures sufficient to produce an amine-aldehyde adduct product having a specific gravity between about 3% and 7% less than the specific gravity of a mixture of starting materials, where the amine comprises compounds of the general formula $R^1R^2NH$, where $R^1$ and $R^2$ are hydrogen atoms or carbyl groups, where $R^1$ and $R^2$ groups are not both a hydrogen atom and the carbyl groups have between 1 and 20 carbon atoms where one or more carbon atoms can be replaced by one or more hetero atoms selected from the group consisting of boron, nitrogen, oxygen, phosphorus, sulfur or mixture or combinations thereof and where one or more of the hydrogen atoms can be replaced by one or more single valence atoms selected from the group consisting of fluorine, chlorine, bromine, iodine or mixtures or combinations thereof and the alcohol comprises a linear or branched alcohol having from one to 20 carbon atoms, where one or more carbon atoms can be replaced by one or more hetero atoms selected from the group consisting of boron, nitrogen, oxygen, phosphorus, sulfur or mixture or combinations thereof and where one or more of the hydrogen atoms can be replaced by one or more single valence atoms selected from the group consisting of fluorine, chlorine, bromine, iodine or mixtures or combinations thereof.

2. The method of claim 1, wherein the specific gravity between about 4% and 6% less than the specific gravity of the mixture of starting materials.

3. The method of claim 1, wherein the reaction time is between about 5 hours and about 12 hours.

4. The method of claim 1, wherein the reaction time is between about 9.5 hours and about 12 hours.

5. The method of claim 1, wherein the reaction temperature is between about 85° C. and about 95° C.

6. The method of claim 1, wherein the time is between about 5 hours and about 12 hours and the reaction temperature is between about 85° C. and about 95° C.

7. The method of claim 1, wherein the time is between about 9.5 hours and about 12 hours and the reaction temperature is between about 85° C. and about 95° C.

8. The method of claim 1, wherein the product has a pH between about 6.2 and about 9.0.

9. The method of claim 1, wherein the aldehyde comprises formaldehyde.

10. The method of claim 9, wherein the reaction time is less than 13.5 hours.

11. The method of claim 9, wherein the amine comprises dibutyl amine.

12. The method of claim 11, wherein the specific gravity of the product is between 0.828 and 0.860.

13. The method of claim 11, wherein the reaction time is less than 13.5 hours, provided the specific gravity is between 0.828 and 0.860 and the reaction temperature is between about 85° C. and about 95° C.

14. The method of claim 1, the product does not form solids or gels upon exposure to fluids or gases containing noxious sulfur species, and in the case of formaldehyde-amine, adduct products, the products have no detectable formaldehyde and are non-foaming.

15. The method of claim 1, wherein the product has a sulfur scavenging activity at least one fold greater than a composition prepared with an amine to aldehyde ratio greater than or less than the ratio between about 0.8 and about 0.45.

16. The method of claim 1, wherein the ratio is about 0.5.

17. The method of claim 16, wherein the product has a sulfur scavenging activity at least one fold greater than a composition prepared with an amine to aldehyde ratio greater than or less than the ratio of about 0.5.

18. An amine-aldehyde adduct composition comprising a reaction product of an amine containing component and an aldehyde containing component prepared in the presence of an alcohol at an amine to aldehyde ratio of between about 0.8 and 0.45 for a reaction time and at a reaction temperatures sufficient to produce an amine-aldehyde adduct product having a specific gravity between about 3% and 7% less than the specific gravity of a true mixture of starting materials, where the amine comprises compounds of the general formula $R^1R^2NH$, where $R^1$ and $R^2$ are hydrogen atoms or carbyl groups, where $R^1$ and $R^2$ group are not both a hydrogen atom and the carbyl groups have between 1 and 20 carbon atoms where one or more carbon atoms can be replaced by one or more hetero atoms selected from the group consisting of boron, nitrogen, oxygen, phosphorus, sulfur or mixture or combinations thereof and where one or more of the hydrogen atoms can be replaced by one or more single valence atoms selected from the group consisting of fluorine, chlorine, bromine, iodine or mixtures or combinations thereof and the alcohol comprises a linear or branched alcohol having from one to 20 carbon atoms, where one or more carbon atoms can be replaced by one or more hetero atoms selected from the group consisting of boron, nitrogen, oxygen, phosphorus, sulfur or mixture or combinations thereof and where one or more of the hydrogen atoms can be replaced by one or more single valence atoms selected from the group consisting of fluorine, chlorine, bromine, iodine or mixtures or combinations thereof.

19. The composition of claim 18, wherein the specific gravity between about 4% and 6% less than the specific gravity of the mixture of starting materials.

20. The composition of claim 18, wherein the reaction time is between about 5 hours and about 12 hours.

21. The composition of claim 18, wherein the reaction time is between about 9.5 hours and about 12 hours.

22. The composition of claim 18, wherein the reaction temperature is between about 85° C. and about 95° C.

23. The composition of claim 18, wherein the neat composition has a pH between about 6.2 and about 9.0.

24. The method of claim 1, wherein the aldehyde comprises formaldehyde.

25. The method of claim 9, wherein the amine comprises dibutyl amine.

26. The method of claim 25, wherein the specific gravity of the product is between 0.828 and 0.860.

27. The method of claim 25, wherein the reaction time is less than 13.5 hours, provided the specific gravity is between 0.828 and 0.860 and the reaction temperature is between about 85° C. and about 95° C.

28. The composition of claim 18, the product does not form solids or gels upon exposure to fluids or gases containing noxious sulfur species, and in the case of formaldehyde-amine, adduct products, the products have no detectable formaldehyde and are non-foaming.

29. The composition of claim 18, wherein the composition has a sulfur scavenging activity at least one fold greater than a composition prepared with an amine to aldehyde ratio greater than or less than the ratio between about 0.8 and about 0.45.

30. The composition of claim 18, wherein the ratio is about 0.5.

31. The composition of claim 18, wherein the composition has a sulfur scavenging activity at least one fold greater than a composition prepared with an amine to aldehyde ratio greater than or less than the ratio of about 0.5.

* * * * *